(12) United States Patent
Fotouhi et al.

(10) Patent No.: US 7,132,421 B2
(45) Date of Patent: Nov. 7, 2006

(54) CIS-IMIDAZOLES

(75) Inventors: Nader Fotouhi, Basking Ridge, NJ (US); Emily Aijun Liu, Basking Ridge, NJ (US); Binh Thanh Vu, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 164 days.

(21) Appl. No.: 10/868,092

(22) Filed: Jun. 15, 2004

(65) Prior Publication Data

US 2004/0259867 A1 Dec. 23, 2004

Related U.S. Application Data

(60) Provisional application No. 60/553,215, filed on Mar. 15, 2004, provisional application No. 60/479,563, filed on Jun. 17, 2003.

(51) Int. Cl.
*A61K 31/5375* (2006.01)
*A61K 31/454* (2006.01)
*A61K 31/496* (2006.01)
*C07D 401/14* (2006.01)
*C07D 403/02* (2006.01)

(52) U.S. Cl. .............. 514/235.8; 514/252.14; 514/326; 514/399; 544/122; 544/370; 546/210; 548/334.1

(58) Field of Classification Search .......... None
See application file for complete search history.

(56) References Cited

U.S. PATENT DOCUMENTS

6,593,353 B1 * 7/2003 Gudkov et al. ............. 514/367
6,734,302 B1 * 5/2004 Kong et al. ................ 544/139

FOREIGN PATENT DOCUMENTS

| EP | 363 061 | 4/1990 |
| EP | 433 682 | 6/1991 |
| WO | WO 00/78725 | 12/2000 |
| WO | WO 03/051359 | 6/2003 |
| WO | WO 03/051360 | 6/2003 |

* cited by examiner

*Primary Examiner*—Golam M. M. Shameem
*Assistant Examiner*—Andrew B. Freistein
(74) *Attorney, Agent, or Firm*—George W. Johnston; Patricia S. Rocha-Tramaloni; David E. Wildman

(57) ABSTRACT

The present invention provides compounds according to formula I and pharmaceutically acceptable salts and esters thereof, having the designations provided herein and which inhibit the interaction of MDM2 protein with a p53-like peptide and have antiproliferative activity

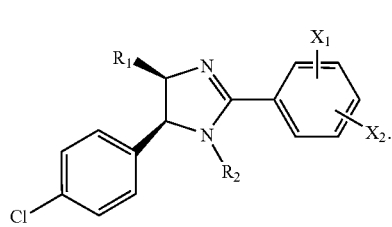

12 Claims, No Drawings

CIS-IMIDAZOLES

PRIORITY TO RELATED APPLICATION

This application claims the benefit of Provisional Applications Ser. No. 60/479,563, filed Jun. 17, 2003 and Ser. No. 60/553,215, filed Mar. 15, 2004.

FIELD OF THE INVENTION

This invention is related to at least one compound selected from a compound of formula I

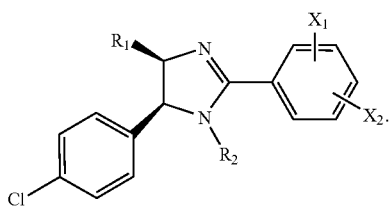

and the pharmaceutically acceptable salts and esters thereof, wherein $X_1$, $X_2$, $R_1$ and $R_2$ are described within this application. This compound is believed to inhibit the interaction of MDM2 protein with a p53-like peptide and have anti-proliferative activity

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.*, 1972, 37, 2158–2161, report synthesis of imidazolines. Hunter et al. *Can. J. Chem.*, 1972, Vol. 50, 669–77, report the preparation of amarine and isoamarine compounds which had previously been studied for chemiluminescence (McCapra et al. *Photochem. and Photobiol.* 1965, 4, 1111–1121). Zupanc et al. *Bull. Soc. Chem. & Tech.* (Yugoslavia) 1980–81, 27/28, 71–80, report the use of triaryl imidazolines as starting materials in the preparation of EDTA derivatives. EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

SUMMARY OF THE INVENTION

The present invention is directed to at least one compound selected from a compound a compound of formula I

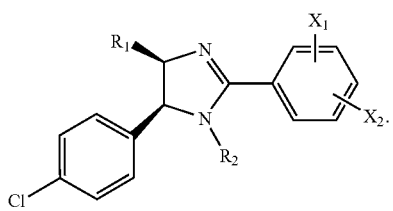

wherein $X_1$ and $X_2$ are each independently selected from the group consisting of hydrogen, $-OR_3$, $-SR_4$, $-NR_5R_6$, $-CONR_7R_8$, $-COOR_9$, halogen, nitro, trifluoromethyl, lower alkyl, lower alkyl substituted by $R_{10}$ and cycloalkyl;

$R_1$ is selected from the group consisting of C1-C8 alkyl; C1-C4 alkyl attached to C4-C8 cycloalkyl; and C4-C8 cycloalkyl;

$R_2$ is $-C=OR_9$;

$R_3$ is selected from the group consisting of hydrogen, lower alkyl, lower alkyl substituted by $R_8$, and cycloalkyl;

$R_4$ is selected from the group consisting of hydrogen and lower alkyl;

$R_5$ and $R_6$ are each independently selected from the group consisting of hydrogen, lower alkyl and cycloalkyl; or $R_5$ and $R_6$ together with the two carbon atoms and the bonds between them from the benzene ring to which they are substituted form a ring selected from a 5- or 6-membered unsaturated ring or a 5- or 6-membered saturated ring that contains at least one hetero atom selected from S, N and O;

$R_7$ is selected from the group consisting of hydrogen, lower alkyl and cycloalkyl;

$R_8$ is selected from the group consisting of $-CONR_5R_6$, $-NR_5R_6$, $COOR_7$, aryl, halogen, lower alkoxy, morpholinyl and heterocycles;

$R_9$ is selected from C1–C4 alkyl, $-CH=CHCOOH$, $-NHCH_2CH_2R_{10}$, $-N(CH_2CH_2OH)CH_2CH_2OH$, $-N(CH_3)CH_2CH_2NCH_3$, $-N(CH_3)CH_2CH_2N(CH_3)$ $CH_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C=O—$R_{11}$, —OH, lower alkyl substituted with hydroxy, lower alkyl substituted with —$NH_2$, N-lower alkyl, —$SO_2CH_3$, =O, —$CH_2C$=$OCH_3$, and 5- and 6-membered saturated rings containing at least one hetero atom selected from S, N and O;

$R_{10}$ is selected from —$N(CH_3)CH_3$, —$NHCH_2CH_2NH_2$, —$NH_2$, morpholinyl and piperazinyl; and $R_{11}$ is selected from H, lower alkyl, —$NH_2$, —N-lower alkyl, lower alkyl substituted with hydroxy, and lower alkyl substituted with $NH_2$, or a pharmaceutically acceptable salt or ester thereof.

DETAILED DESCRIPTION OF THE INVENTION

The present invention is directed to at least one compound selected from a compound of formula I

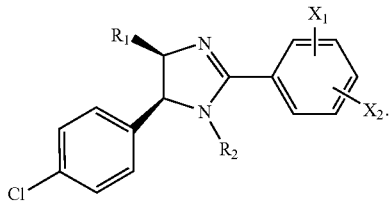

I and the pharmaceutically acceptable salts and esters thereof, wherein $X_1$ and $X_2$ are each independently selected from the group consisting of hydrogen, —$OR_3$, —$SR_4$, —$NR_5R_6$, —$CONR_7R_8$, —$COOR_9$, halogen, nitro, trifluoromethyl, lower alkyl, lower alkyl substituted by $R_{10}$, cycloalkyl;

$R_1$ is selected from the group consisting of C1–C8 alkyl, C1–C4 alkyl attached to C4–C8 cycloalkyl, and C4–C8 cycloalkyl;

$R_2$ is —C=$OR_9$;

$R_3$ is selected from the group consisting of hydrogen, lower alkyl, lower alkyl substituted by $R_8$, and cycloalkyl;

$R_4$ is selected from the group consisting of hydrogen and lower alkyl;

$R_5$ and $R_6$ are each independently selected from the group consisting of hydrogen, lower alkyl and cycloalkyl; or $R_5$ and $R_6$ together with the two carbon atoms and the bonds between them from the benzene ring to which they are substituted form a ring selected from a 5- or 6-membered unsaturated ring or a 5- or 6-membered saturated ring that contains at least one hetero atom selected from S, N and O;

$R_7$ is selected from the group consisting of hydrogen, lower alkyl and cycloalkyl;

$R_8$ is selected from the group consisting of —$CONR_5R_6$, —$NR_5R_6$, $COOR_7$, aryl, halogen, lower alkoxy, morpholinyl and heterocycles;

$R_9$ is selected from C1–C4 alkyl, —CH=CHCOOH, —$NHCH_2CH_2R_{10}$, —$N(CH_2CH_2OH)CH_2CH_2OH$, —$N(CH_3)CH_2CH_2NCH_3$, —$N(CH_3)CH_2CH_2N(CH_3)CH_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C=O—$R_{11}$, —OH, lower alkyl substituted with hydroxy, lower alkyl substituted with —$NH_2$, N-lower alkyl, —$SO_2CH_3$, =O, —$CH_2C$=$OCH_3$, and 5- and 6-membered saturated rings containing at least one hetero atom selected from S, N and O;

$R_{10}$ is selected from —$N(CH_3)CH_3$, —$NHCH_2CH_2NH_2$, —$NH_2$, morpholinyl and piperazinyl; and $R_{11}$ is selected from H, lower alkyl, —$NH_2$, —N-lower alkyl, lower alkyl substituted with hydroxy, and lower alkyl substituted with $NH_2$, or a pharmaceutically acceptable salt or ester thereof.

When $R_2$=H, the compounds of the formula I may exist as a mixture of 2 stereoisomers IA and IB. Therefore, this invention includes these 2 isomers (when $R_2$=H). The cis isomers of I are preferred.

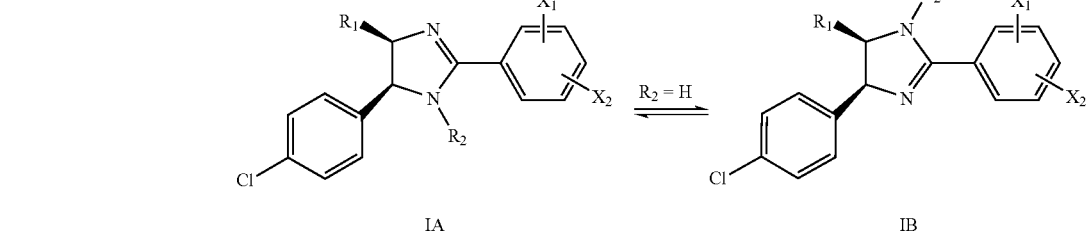

IA                    IB

When $R_2 \neq H$, the compounds of the formula I is a racemic mixture of two enantiomers. Therefore, this invention also includes these enantiomers.

Preferably, R1 is $C_1$–$C_8$ alkyl, $C_1$–$C_4$ alkyl attached to $C_4$–$C_8$ cycloalkyl. $X_1$ is selected from the group consisting of ethoxy, isopropoxy, 2-fluoroethoxy and —$OCH_2CF_3$ at the ortho position. $X_2$ is selected from the group consisting of methoxy, ethoxy and trifluoromethyl at the para position. The compound of claim 1 wherein $R_9$ is selected from morpholinyl, piperazinyl, piperadinyl, cyclopentyl, cyclohexyl, thiophenyl, isoxazlyl and furanyl, piperazinyl substituted with at least one group selected from C1–C3 alkyl, —C1–C2 alkoxy, —C=$OCH_3$, —$SO_2CH_3$, —C=O, —OH, —$CH_2NH_2$, —C=$OCH_2NH_2$, —C=$OCH_2OH$, —C=OC(OH)$CH_2OH$, —$CH_2C(OH)$—$CH_2OH$, —C=ON($CH_2$—$)_2$, —C=ONH2, —C=ON($CH_3$)$CH_3$, —C=OCH($CH_3$)$_2$, —$CH_2C$=$OCH_3$, —$CH_2CH(OH)CH_3$, —CH($CH_3$)CH(OH)$CH_3$ and piperidinyl substituted with at least one group selected from C1–C3 alkyl, —C1–C2 alkoxy, —C=$OCH_3$, —$SO_2CH_3$, —C=O, —OH, —$CH_2NH_2$, —C=$OCH_2NH_2$, —C=$OCH_2OH$, —C=OC (OH)CH$_2$OH, —CH$_2$C(OH)CH$_2$OH, —C=ON(CH$_2$)$_2$, —C=ONH$_2$, and —C=ON(CH$_3$)CH$_3$, —N(CH$_3$)CH$_3$, pyrrolidinyl and piperadinyl.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"IC$_{50}$" refers to the concentration of a particular compound required to inhibit 50% of a specific measured activity. IC$_{50}$ can be measured, inter alia, as is described subsequently.

"Alkyl" denotes a straight-chained or branched saturated aliphatic hydrocarbon. "Lower alkyl" groups denote C1–C6 alkyl groups and include methyl, ethyl, propyl, isopropyl, butyl, t-butyl, 2-butyl, pentyl, hexyl, and the like. Generally, lower alkyl is preferably C1–C4 alkyl, and more preferably C1–C3 alkyl.

"Cycloalkyl" means a non-aromatic, partially or completely saturated cyclic aliphatic hydrocarbon group containing 3 to 8 atoms.

"Heterocycle" means a 3 to 10 member saturated or partially saturated non-aromatic monovalent cyclic radical having from 1 to 3 heteroatoms selected from nitrogen, oxygen or sulfur, or a combination thereof.

"Alkoxy" denotes —O-alkyl. "Lower alkoxy" denotes —O-lower alkyl.

"Saturated 4-, 5- and 6-membered rings" refers to cycloalkyl structures having 4, 5 and 6 carbons on the ring structure, respectively. Specifically, they refer to cyclobutyl, cyclopentyl and cyclohexyl respectively.

"Saturated or unsaturated 5- and 6-membered rings containing at least one hetero atom wherein the hetero atom is selected from S, N and O" refers to a cyclic structure having 5 and 6 carbons on the ring respectively, such that the ring may be saturated or unsaturated, and wherein seach such structure contains one or two hetero atoms. Examples of saturated or unsatureated 5- and 6-membered rings containing at least one hetero atom wherein the hetero atom is selected from S, N and O are pyrrolidine, piperidine, piperazine, morpholine, pyrrole, and imidazole.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

A "therapeutically effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

The present invention is also directed to a pharmaceutical compositon which comprises a compound of formula I, or a pharmaceutically acceptable salt or ester thereof, and a pharmaceutically acceptable carrier. Additionally, the present inveiton is directed to a method of treating a disease based on the interaction of MDM2 protein with a p53-like peptide comprising administering to a patient in need of such treatment a therapeutically effective amount of at least one compound of formula I or a pharmaceutically acceptable salt or ester thereof.

The compounds of the present invention can be prepared according to the following schemes. The following definitions are provided as applicable to the synthesis schemes:

Synthesis

The compounds of formula I can be prepared according to the scheme 1.

Scheme 1

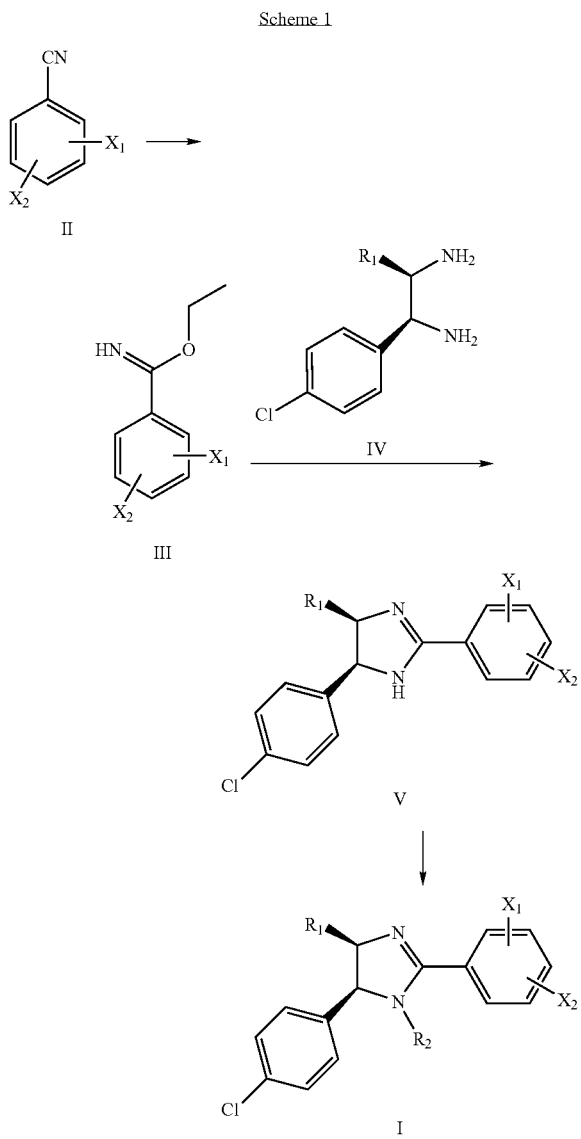

Many benzonitriles of formula II are commercially available. They are converted to the imidate salts (III) using HCl gas in ethanol. The rate of the reaction depends on the substituents on the phenyl ring. In cases where $X_1$ or $X_2 \neq H$, it may be necessary to run the reaction under pressure of HCl over a longer period of time. Condensation of the imidates (III) with the 1,2-diamines (IV) is carried out in ethanol at 40–100° C. in the presence or absence of a base such as triethylamine.

If it is desired to prepare the compounds of formula II which are not commercially available, many synthetic methods known in the art can be employed. Suitable processes for synthesizing these benzonitriles are provided in the examples. Following schemes illustrate some of these methods.

A compound of formula B ($V^{16}$ can be any suitable group such as $V^1$, $V^2$, $V^3$, $V^4$, or $V^5$) can be prepared by alkylation of a compound of formula A with $V^6X$ (X=Cl, Br, I) using conventional methods (scheme V). The phenoxide anion is generated by a base such as cesium carbonate or potassium carbonate. The reaction typically is carried out in refluxing acetone. $V^6$ can also be introduced using Mitsunobu reaction (see for example, Hughes, D. L. Org. React. 1992, 42, 335–656).

Scheme 1a

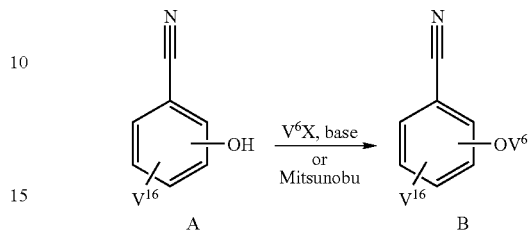

A compound of formula C ($V^{16}$ can be any suitable group such as $V^1$, $V^2$, $V^3$, $V^4$, or $V^5$) can be converted into the benzonitrile D using literature procedures (Karmarkar, S. N; Kelkar, S. L.; Wadia, M. S. Synthesis 1985, 510–512; Bergeron, R. J. et al. J. Med. Chem. 1999, 42, 95–108). V group can then be introduced using $V^6X$ (X=Cl, Br, I) or Mitsunobu reaction to give the benzonitrile 13 (scheme 1b).

Scheme 1b

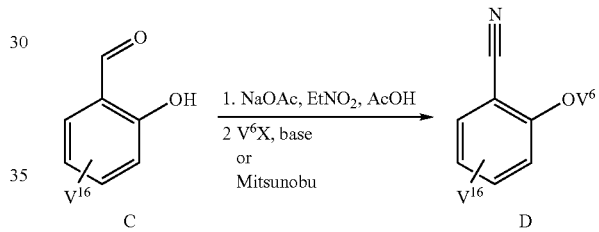

A compound of formula F can be prepared by bromination or iodination of phenol E (Scheme VII), ($V^{16}$ can be any suitable group such as $V^1$, $V^2$, $V^3$, $V^4$, or $V^5$). Reaction conditions such as N-bromosuccinamide/tetrahydrofuran or iodine/thallium(I) acetate can be utilized (see for example, Carreno, M. C.; Garcia Ruano, J. L.; Sanz, G.; Toledo, M. A.; Urbano, A. Synlett 1997, 1241–1242; Cambie, R. C.; Rutledge, P. S.; Smith-Palmer, T.; Woodgate, P. D. J. Chem. Soc., Perkin Trans. 1 1976, 1161–4). $V^5$ group can then be introduced using $V^6X$ (X=Cl, Br, I) or Mitsunobu reaction. Methods of converting aromatic halides to the corresponding nitriles are known in the art (see for example, Okano, T.; Iwahara, M.; Kiji, J., Synlett 1998, 243). Cyanation of the halide (X'=Br, I) can be accomplished using zinc cyanide with a catalyst such as tetrakis(triphenylphosphine)palladium (0). Solvents such dimethylformamide can be used and the reaction temperature is between 80–110 C.

Scheme 1c

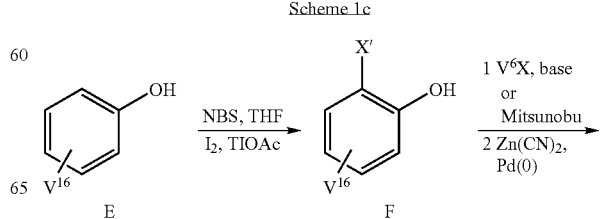

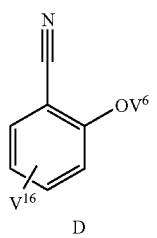

D

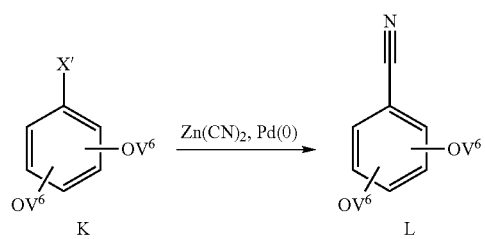

In scheme 1D, amination of aromatic halide G using HNV[7]V[8] and palladium catalyst can be utilized to provide the benzonitrile of formula H (see for example, Harris, M. C.; Geis, O.; Buchwald, S. L. *J. Org. Chem*. 1999, 64, 6019).

Scheme 1d

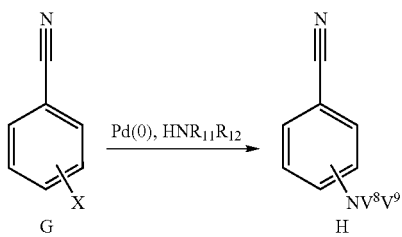

A compound of formula D ($V^{16}$ can be any suitable group such as $V^1$, $V^2$, $V^3$, $V^4$, or $V^5$) can be prepared by nucleophilic substitution of 2-halobenzonitrile I (scheme 1e). (see for example, X=F: Wells, K. M.; Shi, Y.-J.; Lynch, J. E.; Humphrey, G. R.; Volante, R. P.; Reider, P. J. *Tetrahedron Lett*. 1996, 37, 6439–6442; X=NO$_2$: Harrison, C. R.; Lett, R. M.; McCann, S. F.; Shapiro, R.; Stevenson, T. M. WO 92/03421, 1992).

Scheme 1e

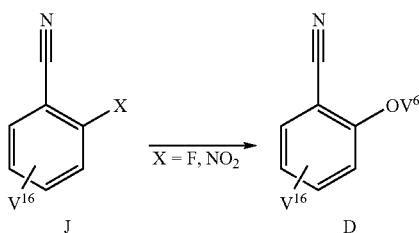

To prepare the benzonitrile of formula L wherein $V^1$, $V^2$, $V^3$, $V^4$, or $V^5$=OV$^6$, sequential alkylation of the diol 19 with suitable V$^6$X (X=Cl, Br, I) are used. The bromides K are then converted to the nitriles L using zinc cyanide and Pd(0) catalyst (scheme 1f).

Scheme 1f

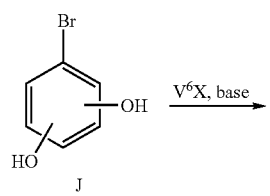

The 1,2-diamines of formula IV are prepared using procedures as reported by Shatzmiller, S.; Bercovici, S. *Liebigs Ann. Chem*. 1992, 1005–1009 (Scheme 2). The ketone VI is converted to the corresponding oxime ether. α-Bromination of the oxime ether with N-bromosuccinimide and reaction of the α-bromo oxime ether with ammonia in methanol gives the α-amino oxime ether VII. Reduction of VII with lithium aluminum hydride gives a mixture of cis and trans 1,2-diamine (~4–6:1 ratio of cis:trans). The crude 1,2-diamine is then reacted with compound of formula III to give a mixture of cis and trans products. The desired compound (formula V) can be isolated from the mixture by preparative chromatography techniques.

Scheme 2

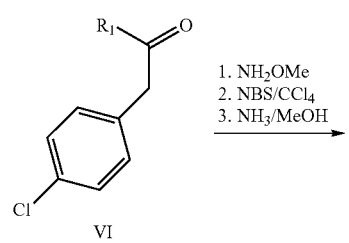

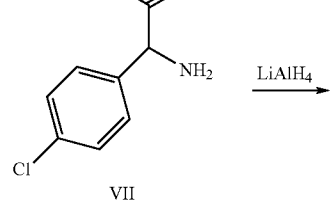

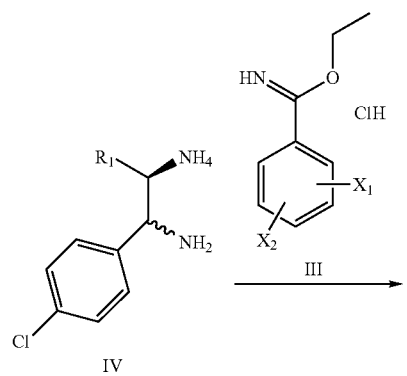

-continued

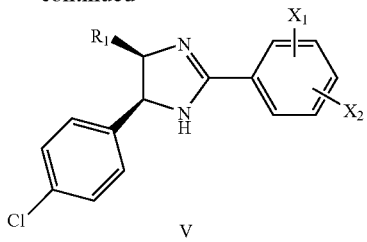

V

When $R_2$=$COR_{11}$, the compound V is converted to the compound of formula VIII using a compound of formula ClCOR$_{11}$ (a known compound or a compound prepared by known methods) in the presence of a base such triethylamine (Scheme 3).

Scheme 3

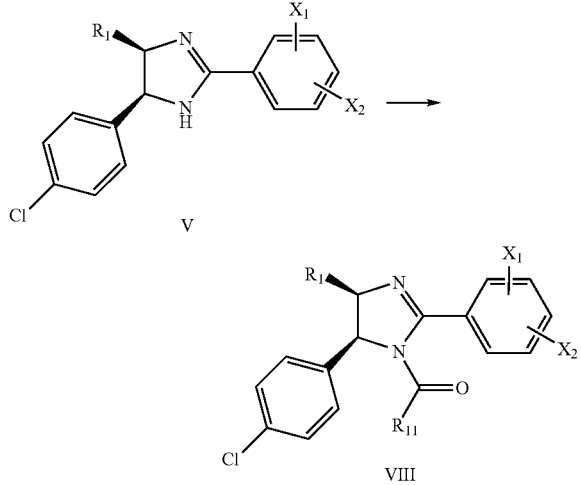

When $R_2$=$CONR_{12}R_{13}$, the compound of formula V is reacted with phosgene at 0° C. in the presence of a base such as triethylamine followed by the treatment of a compound of formula NHR$_{12}$R$_{13}$ (a known compound or a compound prepared by known methods) to give the compound of formula IX (Scheme 4).

Scheme 4

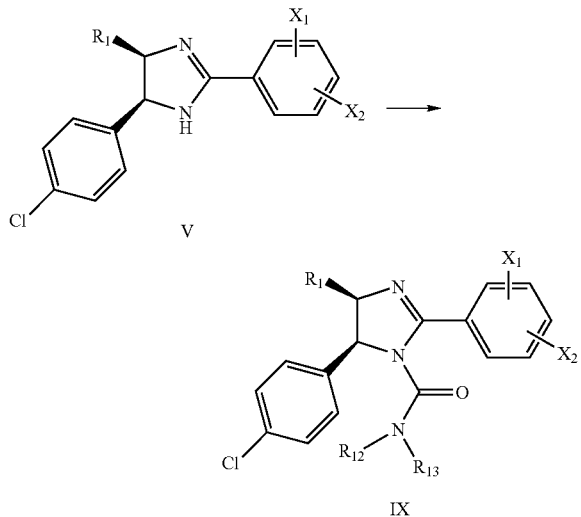

The present invention encompasses the following Examples. Structural formulas follow. With regard to structural formulas, it is understood that oxygen and nitrogen atoms with available electrons have a hydrogen bound thereto, as indicated by compound name.

The following compounds were tested according to the above-described assay and exhibited IC$_{50}$'s from about 0.5 µM to about 300 µM.

EXAMPLE 1

Ethyl 2-ethoxy-4-methoxy-benzimidate hydrochloride

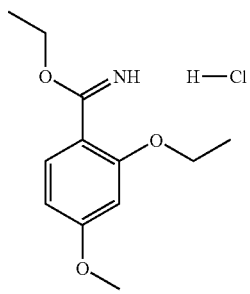

A mixture of the 2-hydroxy-4-methoxybenzaldehyde (20 g, 128.8 mmol), sodium acetate (35.05 g, 257.6 mmol) and nitroethane (19 mL, 257.6 mmol) in glacial acetic acid (100 mL) was heated at gentle reflux for 12 h. The reaction mixture was then poured into ~1000 mL of ice water (1:1 ratio of ice and water). The product was extracted with ethyl acetate (3×200 mL). The organic extracts were washed with sodium bicarbonate solution until the aqueous layer had pH ~8. The organic layers were then dried over anhydrous magnesium sulfate and concentrated in vacuo to afford 2-hydroxy-4-methoxy-benzonitrile as a yellow oil (16.5 g, 86%). It was used without further purification.

To a solution of 2-hydroxy-4-methoxy-benzonitrile (9.637 g, 64.61 mmol) in ethanol (50 mL) were added potassium carbonate (17.88 g, 129.2 mmol) and iodoethane (15.7 mL, 193.8 mmol). The reaction mixture was heated at gentle reflux for 12 h. The solvent was removed to afford a yellow-brown paste. It was then taken in diethyl ether (50 mL) and water (20 mL). The layers were separated and the aqueous layer was extracted with diethyl ether (2×150 mL). The combined organic extracts were washed with water (1×20 mL), brine (1×20 mL), and dried over anhydrous sodium sulfate. The solids were then filtered off, and the filtrate was concentrated in vacuo. Purification of the crude residue by flash chromatography (Biotage system, KP-Sil™ 32–63 µm, 60 Å silica gel) eluting with 10–15% ethyl acetate in hexanes yielded 2-ethoxy-4-methoxy-benzonitrile as yellow solids (9.487 g, 83%).

Hydrogen chloride gas was passed through a solution of 2-ethoxy-4-methoxy-benzonitrile (6.3 g, 35.55 mmol) in anhydrous ethanol (70 mL) cooled to −10° C. After 30 min, hydrogen chloride gas was stopped and the reaction mixture was stirred at room temperature in a closed reaction vessel for 4 d. The reaction vessel was cooled to 0° C. before the stopper was removed. Argon gas was passed through the solution to remove excess hydrogen chloride gas. The solvent was evaporated and the residue was triturated in diethyl ether (100 mL) to afford ethyl 2-ethoxy-4-methoxy-benzimidate hydrochloride (7.3 g, 79%). It was used without further purification.

EXAMPLE 2

The following compounds were prepared in a manner analogous to that described in Example 1:

(a) Ethyl 2-isopropoxy-4-methoxy-benzimidate hydrochloride from 2-hydroxy-4-methoxy-benzonitrile and isopropyl iodide.

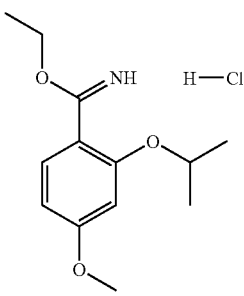

(b) Ethyl 2-(2-fluoro-ethoxy)-4-methoxy-benzimidate hydrochloride from 2-hydroxy-4-methoxy-benzonitrile and 1-bromo-2-fluoro-ethane.

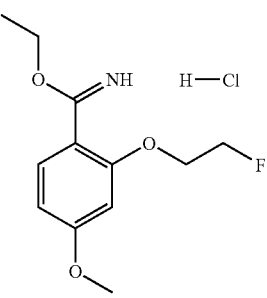

(c) Ethyl 2,4-diethoxy-benzimidate hydrochloride from 2,4-diethoxy-benzaldehyde.

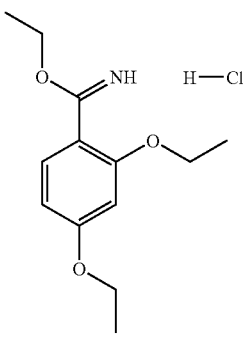

EXAMPLE 3

1-(4-Chloro-phenyl)-3-cyclopentyl-propan-1-one

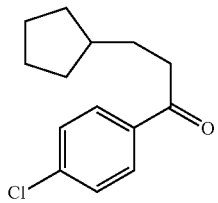

Aluminum chloride (4.979 g, 37.34 mmol) was added in small portions to a solution of 3-cyclopentylpropionyl chloride (3 g, 18.67 mmol) in 1,2-dichloroethane (100 mL) cooled to 0° C. After 15 min., chlorobenzene (6.304 g, 56.01 mmol) was added. The reaction mixture was stirred at 0° C. for 1 h and at room temperature for 48 h. It was then poured into a mixture of ice and water. The product was extracted with ethyl acetate. The organic layers were washed with saturated solution of sodium bicarbonate (1×30 mL), brine (1×20 mL) and dried over anhydrous magnesium sulfate. The solids were then filtered off, and the filtrate was concentrated in vacuo. Purification of the crude residue by flash chromatography (Biotage system, KP-Sil™ 32–63 μm, 60 Å silica gel) eluting with hexanes yielded 1-(4-chloro-phenyl)-3-cyclopentyl-propan-1-one (1.12 g, 25%) as yellow oil.

EXAMPLE 4

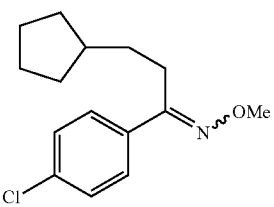

1-(4-Chloro-phenyl)-3-cyclopentyl-propan-1-one O-methyl-oxime

To a solution of 1-(4-chloro-phenyl)-3-cyclopentyl-propan-1-one (1.12 g, 4.731 mmol) in ethanol (15 mL) was added potassium carbonate (1.962 g, 14.19 mmol) and methoxyamine hydrochloride (494 mg, 5.914 mmol). The reaction mixture was heated at reflux for 12 h. Upon cooling to room temperature, the reaction mixture was filtered, and the white solids were washed with diethyl ether. The filtrate was concentrated in vacuo, and the residue was partitioned between diethyl ether and water. The product was extracted with diethyl ether (2×30 mL). The organic layers were washed with brine and dried over anhydrous sodium sulfate. The solids were then filtered off, and the filtrate was concentrated in vacuo. Purification of the crude residue by flash chromatography (Biotage system, KP-Sil™ 32–63 μm, 60 Å silica gel) eluting with 1–2% ethyl acetate in hexanes yielded 1-(4-chloro-phenyl)-3-cyclopentyl-propan-1-one O-methyl-oxime (762 mg, 61%) as clear oil.

EXAMPLE 5

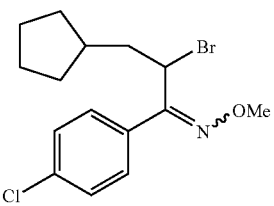

2-Bromo-1-(4-chloro-phenyl)-3-cyclopentyl-propan-1-one O-methyl-oxime

To a solution of 1-(4-chloro-phenyl)-3-cyclopentyl-propan-1-one O-methyl-oxime (1.120 g, 4.214 mmol) in carbon tetrachloride were added N-bromosuccinimide (812 mg, 4.425 mmol) and benzoyl peroxide (102 mg, 0.4 mmol). The resulting mixture was heated at reflux for 12 h. Upon cooling to room temperature, the solids were filtered and washed with diethyl ether. The filtrate was washed with aqueous solution of sodium bicarbonate, sodium thiosulfate and brine. It was then dried with anhydrous sodium sulfate and concentrated in vacuo. Purification of the crude residue by flash chromatography (Biotage system, KP-Sil™ 32–63 µm, 60 Å silica gel) eluting with 1–2% ethyl acetate in hexanes yielded 2-bromo-1-(4-chloro-phenyl)-3-cyclopentyl-propan-1-one O-methyl-oxime (1.16 g, 80%) as yellow oil.

EXAMPLE 6

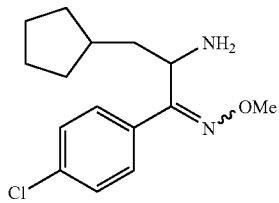

2-Amino-1-(4-chloro-phenyl)-3-cyclopentyl-propan-1-one O-methyl-oxime

The 2-bromo-1-(4-chloro-phenyl)-3-cyclopentyl-propan-1-one O-methyl-oxime (1.16 g, 2.901 mmol) was dissolved in a solution of ammonia in methanol (30 mL, ~7 N). The reaction flask was sealed with a Teflon stopper, and the reaction mixture was stirred at 55–60° C. for 2 d. It was cooled to 0° C. then the stopper was removed. The reaction mixture was concentrated to remove ammonia and methanol. The residue was partitioned between water and diethyl ether. The product was extracted with diethyl ether (2×20 mL). The organic layers were washed with brine, dried over anhydrous sodium sulfate and concentrated in vacuo. Purification of the crude residue by flash chromatography (Biotage system, KP-Sil™ 32–63 µm, 60 Å silica gel) eluting with 50–100% ethyl acetate+0.1% triethylamine in hexanes yielded 2-amino-1-(4-chloro-phenyl)-3-cyclopentyl-propan-1-one O-methyl-oxime (423 mg, 45%) as yellow oil.

EXAMPLE 7

1-(4-Chloro-phenyl)-3-cyclopentyl-propane-1,2-diamine

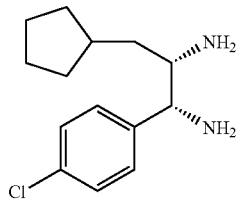

A solution of 2-amino-1-(4-chloro-phenyl)-3-cyclopentyl-propan-1-one O-methyl-oxime (420 mg, 1.567 mmol) in diethyl ether (3 mL) was added dropwise to a slurry mixture of lithium aluminumhydride (307 mg, 7.835 mmol) in diethyl ether (30 mL) cooled to 0° C. At the end of addition, the icebath was removed and the reaction was stirred at room temperature for 3 h. The reaction mixture was cooled to 0° C. and aqueous solution of sodium chloride was added to quench the excess lithium aluminumhydride. Sodium hydroxide solution was added and the biphasic mixture was stirred for 1 h. The product was extracted with diethyl ether (3×30 mL). The ethereal extracts were washed with brine and dried over anhydrous sodium sulfate. Evaporation of the solvent gave 1-(4-chloro-phenyl)-3-cyclopentyl-propane-1,2-diamine as yellow oil (362.7 mg, 96%, 4.3:1.0 ratio of cis:trans). The crude product was used without further purification.

EXAMPLE 8

The following compounds were prepared in a manner analogous to that described in Examples 3–7:

a. 1-(4-Chloro-phenyl)-propane-1,2-diamine

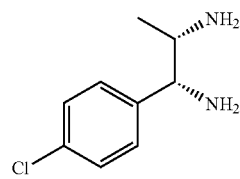

b. 1-(4-Chloro-phenyl)-butane-1,2-diamine

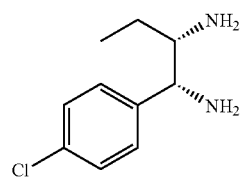

c. 1-(4-Chloro-phenyl)-pentane-1,2-diamine

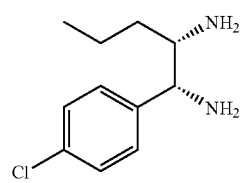

d. 1-(4-Chloro-phenyl)-hexane-1,2-diamine

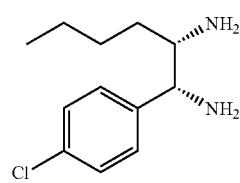

e. 1-(4-Chloro-phenyl)-heptane-1,2-diamine

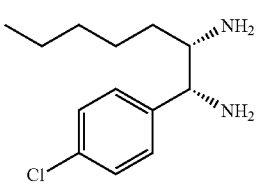

f. 1-(4-Chloro-phenyl)-4-methyl-pentane-1,2-diamine

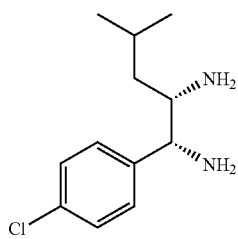

g. 1-(4-Chloro-phenyl)-5-methyl-hexane-1,2-diamine

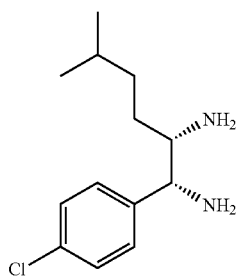

h. 1-(4-Chloro-phenyl)-2-cyclopentyl-ethane-1,2-diamine

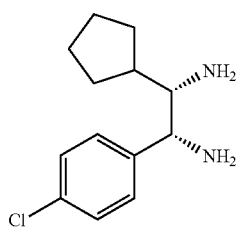

i. 1-(4-Chloro-phenyl)-2-cyclohexyl-ethane-1,2-diamine

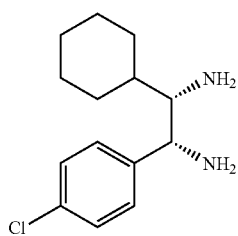

j. 1-(4-Chloro-phenyl)-3-cyclohexyl-propane-1,2-diamine

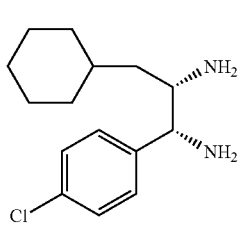

k. 1-(4-Chloro-phenyl)-4-cyclohexyl-butane-1,2-diamine

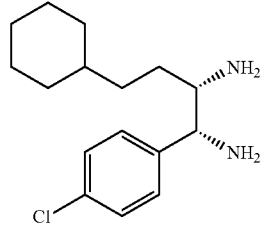

EXAMPLE 9

5-(4-chloro-phenyl)-4-cyclopentylmethyl-2-(2-ethoxy-4-methoxy-phenyl)-4,5-dihydro-1H-imidazole

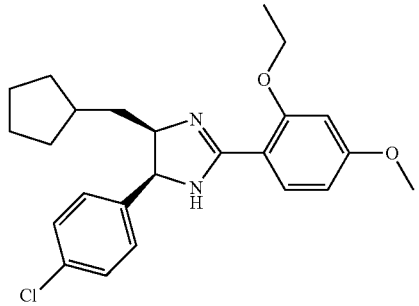

To a solution of 1-(4-chloro-phenyl)-3-cyclopentyl-propane-1,2-diamine (170 mg, 0.672 mmol) and ethyl 2-ethoxy-4-methoxy-benzimidate hydrochloride (210 mg, 0.806 mmol) in ethanol (10 mL) was added triethylamine (82 μL, 0.806 mmol). The reaction mixture was heated at gentle reflux for 6 h. The solvent was removed and the residue was partitioned between water and methylene chloride. The product was extracted with methylene chloride (2×20 mL). The organic layers were washed with brine, dried over anhydrous sodium sulfate and concentrated in vacuo. The residue was purified by flash chromatography (Biotage system, KP-Sil™ 32–63 μm, 60 Å silica gel) eluting with ethyl acetate then 5–10% methanol in ethyl acetate to give 5-(4-chloro-phenyl)-4-cyclopentylmethyl-2-(2-ethoxy-4-methoxy-phenyl)-4,5-dihydro-1H-imidazole (174 mg, 63%, 4.5:1.0 ratio of cis:trans) as a white foam. HR-MS (ES, m/z) observed 413.1993, calculated for $C_{24}H_{30}N_2O_2Cl$ [(M+H)$^+$] 413.1991.

EXAMPLE 10

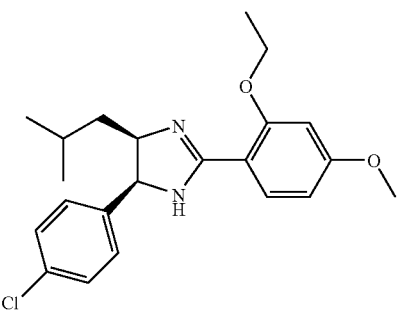

5-(4-Chloro-phenyl)-2-(2-ethoxy-4-methoxy-phenyl)-4-isobutyl-4,5-dihydro-1H-imidazole was prepared from 1-(4- chloro-phenyl)-4-methyl-pentane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 387.1837, calculated for $C_{22}H_{28}N_2O_2Cl$ $[(M+H)^+]$387.1834.

EXAMPLE 11

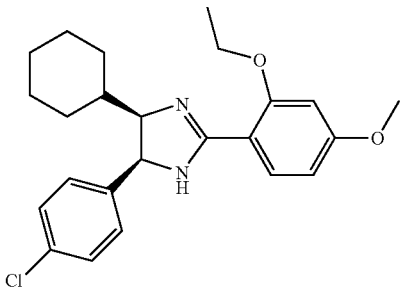

5-(4-Chloro-phenyl)-4-cyclohexyl-2-(2-ethoxy-4-methoxy-phenyl)-4,5-dihydro-1H-imidazole was prepared from 1-(4-chloro-phenyl)-2-cyclohexyl-ethane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 413.1993, calculated for $C_{24}H_{30}N_2O_2Cl$ $[(M+H)^+]$413.1991.

EXAMPLE 12

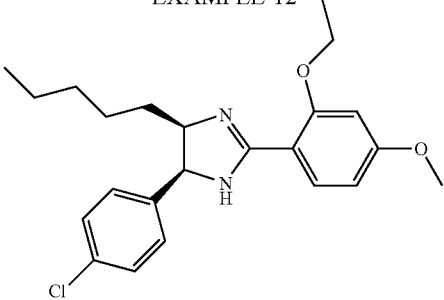

5-(4-Chloro-phenyl)-2-(2-ethoxy-4-methoxy-phenyl)-4-pentyl-4,5-dihydro-1H-imidazole was prepared from 1-(4-chloro-phenyl)-heptane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 401.1993, calculated for $C_{23}H_{30}N_2O_2Cl$ $[(M+H)^+]$401.1991.

EXAMPLE 13

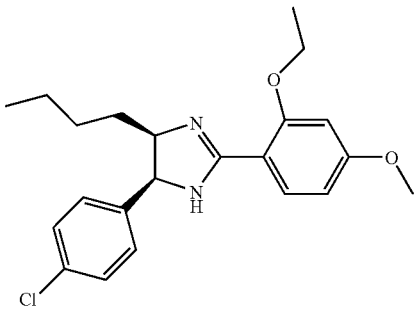

4-Butyl-5-(4-chloro-phenyl)-2-(2-ethoxy-4-methoxy-phenyl)-4,5-dihydro-1H-imidazole was prepared from 1-(4-chloro-phenyl)-hexane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 387.1839, calculated for $C_{22}H_{28}N_2O_2Cl$ $[(M+H)^+]$387.1834.

EXAMPLE 14

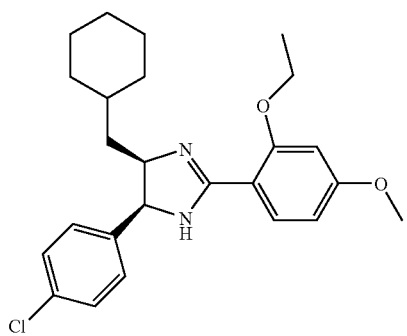

5-(4-Chloro-phenyl)-4-cyclohexylmethyl-2-(2-ethoxy-4-methoxy-phenyl)-4,5-dihydro-1H-imidazole was prepared from 1-(4-chloro-phenyl)-3-cyclohexyl-propane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 427.2150, calculated for $C_{25}H_{32}N_2O_2Cl$ $[(M+H)^+]$427.2147.

EXAMPLE 15

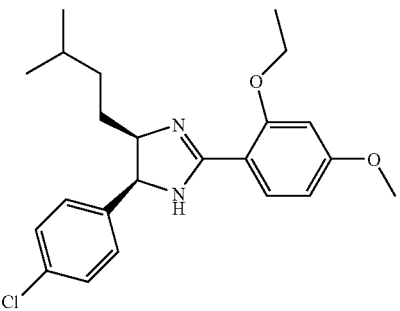

5-(4-Chloro-phenyl)-2-(2-ethoxy-4-methoxy-phenyl)-4-(3-methyl-butyl)-4,5-dihydro-1H-imidazole was prepared from 1-(4-chloro-phenyl)-5-methyl-hexane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 401.1994, calculated for $C_{23}H_{30}N_2O_2Cl$ $[(M+H)^+]$401.1991.

EXAMPLE 16

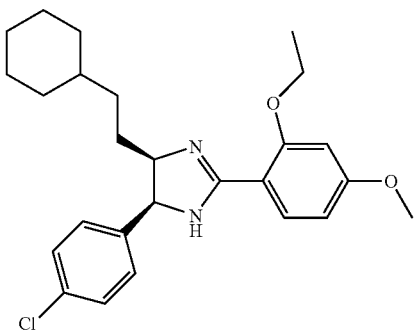

5-(4-Chloro-phenyl)-4-(2-cyclohexyl-ethyl)-2-(2-ethoxy-4-methoxy-phenyl)-4,5-dihydro-1H-imidazole was prepared from 1-(4-chloro-phenyl)-4-cyclohexyl-butane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 441.2309, calculated for $C_{26}H_{34}N_2O_2Cl$ $[(M+H)^+]441.2304$.

EXAMPLE 17

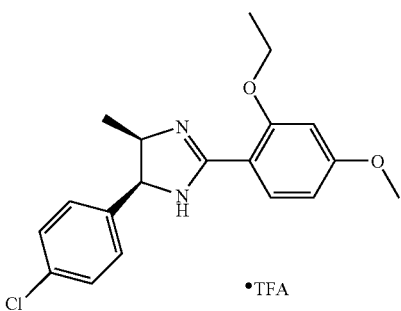

5-(4-Chloro-phenyl)-2-(2-ethoxy-4-methoxy-phenyl)-4-methyl-4,5-dihydro-1H-imidazole, trifluoroacetate salt was prepared from 1-(4-chloro-phenyl)-propane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 345.1366, calculated for $C_{19}H_{22}N_2O_2Cl$ $[(M+H)^+]345.1365$.

EXAMPLE 18

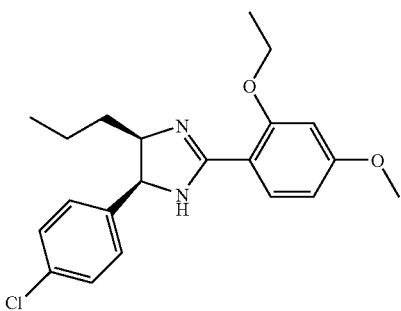

5-(4-Chloro-phenyl)-2-(2-ethoxy-4-methoxy-phenyl)-4-propyl-4,5-dihydro-1H-imidazole was prepared from 1-(4-chloro-phenyl)-pentane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 373.1680, calculated for $C_{21}H_{26}N_2O_2Cl$ $[(M+H)^+]373.1678$.

EXAMPLE 19

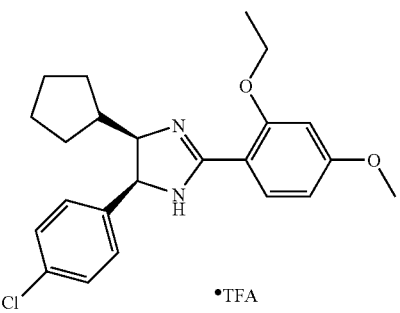

5-(4-Chloro-phenyl)-4-cyclopentyl-2-(2-ethoxy-4-methoxy-phenyl)-4,5-dihydro-1H-imidazole, trifluoroacetate salt was prepared from 1-(4-chloro-phenyl)-2-cyclopentyl-ethane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 399.1834, calculated for $C_{23}H_{28}N_2O_2Cl$ $[(M+H)^+]399.1834$.

EXAMPLE 20

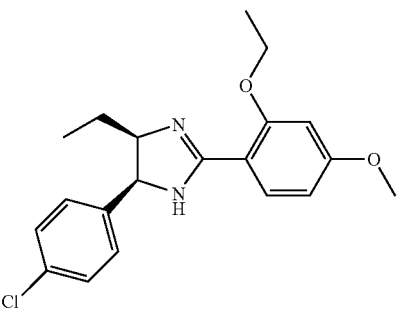

5-(4-Chloro-phenyl)-2-(2-ethoxy-4-methoxy-phenyl)-4-ethyl-4,5-dihydro-1H-imidazole was prepared from 1-(4-chloro-phenyl)-butane-1,2-diamine and ethyl 2-ethoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 359.1524, calculated for $C_{20}H_{24}N_2O_2Cl$ $[(M+H)^+]359.1521$.

EXAMPLE 21

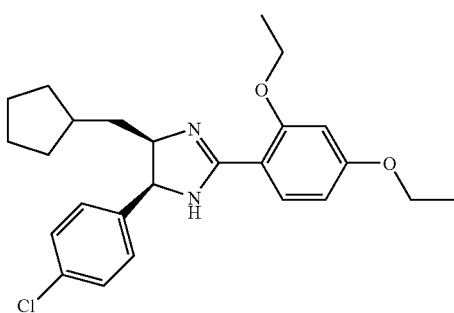

5-(4-Chloro-phenyl)-4-cyclopentylmethyl-2-(2,4-diethoxy-phenyl)-4,5-dihydro-1H-imidazole was prepared from 1-(4-chloro-phenyl)-3-cyclopentyl-propane-1,2-diamine and ethyl 2,4-diethoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 427.2152, calculated for $C_{25}H_{32}N_2O_2Cl$ [(M+H)$^+$]427.2147.

EXAMPLE 22

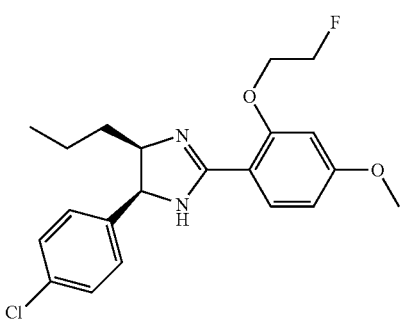

5-(4-Chloro-phenyl)-2-[2-(2-fluoro-ethoxy)-4-methoxy-phenyl]-4-propyl-4,5-dihydro-1H-imidazole was prepared from 1-(4-chloro-phenyl)-pentane-1,2-diamine and ethyl 2-(2-fluoro-ethoxy)-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 391.1587, calculated for $C_{21}H_{25}N_2O_2FCl$ [(M+H)$^+$]391.1583.

EXAMPLE 23

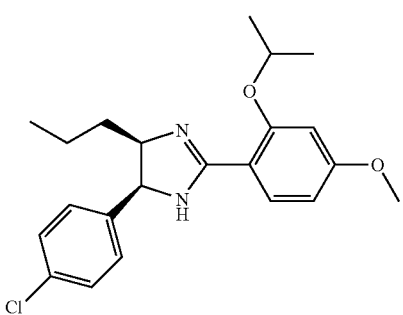

5-(4-Chloro-phenyl)-2-(2-isopropoxy-4-methoxy-phenyl)-4-propyl-4,5-dihydro-1H-imidazole was prepared from 1-(4-chloro-phenyl)-pentane-1,2-diamine and ethyl 2-isopropoxy-4-methoxy-benzimidate hydrochloride in an analogous manner as described for the preparation of 5-(4-chloro-phenyl)-4-cyclopentylmethyl-2-(2-ethoxy-4-methoxy-phenyl)-4,5-dihydro-1H-imidazole (Example 9). HR-MS (ES, m/z) observed 387.1840, calculated for $C_{22}H_{28}N_2O_2Cl$ [(M+H)$^+$]387.1834.

EXAMPLE 24

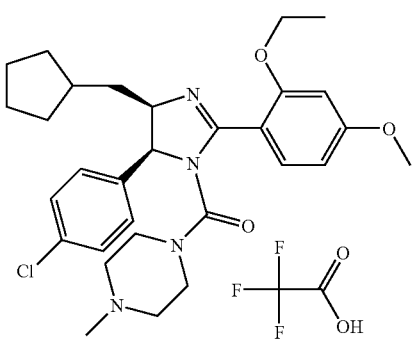

[5-(4-Chloro-phenyl)-4-cyclopentylmethyl-2-(2-ethoxy-4-methoxy-phenyl)-4,5-dihydro-imidazol-1-yl]-(4-methyl-piperazin-1-yl)-methanone, trifluoroacetate salt To a solution of 5-(4-chloro-phenyl)-4-cyclopentylmethyl-2-(2-ethoxy-4-methoxy-phenyl)-4,5-dihydro-1H-imidazole (160 mg, 0.387 mmol) in methylene chloride (15 mL) cooled to 0° C. were sequentially added triethylamine (108 μL, 0.774 mmol) and phosgene (589 μL, 1.161 mmol, 1.97 M in toluene). The reaction mixture was stirred at 0° C. under Argon for 30 min. The solvent and excess reagents were removed by rotovap, and the residue was purified by flash chromatography (Biotage system, KP-Sil™ 32–63 μm, 60 Å silica gel) eluting with 20–25% ethyl acetate in hexanes to give 5-(4-chloro-phenyl)-4-cyclopentylmethyl-2-(2-ethoxy-4-methoxy-phenyl)-4,5-dihydro-imidazole-1-carbonyl chloride (132.6 mg, 72%) as white solids.

A solution of 5-(4-chloro-phenyl)-4-cyclopentylmethyl-2-(2-ethoxy-4-methoxy-phenyl)-4,5-dihydro-imidazole-1-carbonyl chloride (50 mg, 0.105 mmol) in methylene chloride (2 mL) was added to a stirred mixture of 1-methylpiperazine (18 μL, 0.158 mmol) and triethylamine (29 μL, 0.210 mmol) in methylene chloride (3 mL) cooled to 0° C. The reaction mixture was stirred at room temperature for 30 min then concentrated in vacuo. Purification of the crude residue by preparative HPLC (Zorbax $C_{18}$) gave [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (64 mg, 93%, white solids) as trifluoroacetic acid salt. HR-MS (ES, m/z) observed 539.2789, calculated for $C_{30}H_{40}N_4O_3Cl$ [(M+H)$^+$] 539.2784.

EXAMPLE 25

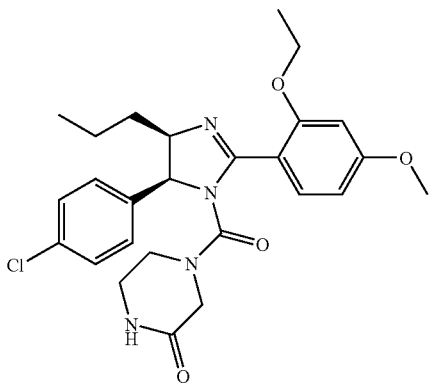

4-[5-(4-Chloro-phenyl)-2-(2-ethoxy-4-methoxy-phenyl)-4-propyl-4,5-dihydro-imidazole-1-carbonyl]-piperazin-2-one was prepared from 5-(4-chloro-phenyl)-2-(2-ethoxy-4-methoxy-phenyl)-4-propyl-4,5-dihydro-1H-imidazole (Example 18) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 499.2113, calculated for $C_{26}H_{32}N_4O_4Cl$ $[(M+H)^+]$499.2107.

EXAMPLE 27

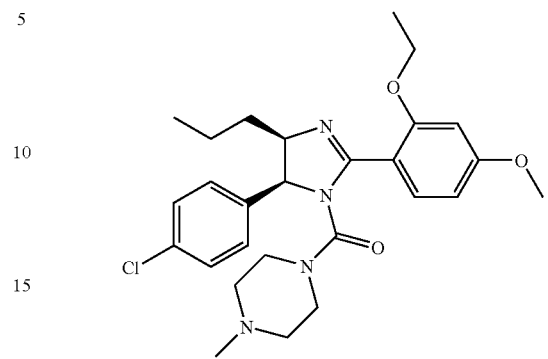

[5-(4-Chloro-phenyl)-2-(2-ethoxy-4-methoxy-phenyl)-4-propyl-4,5-dihydro-imidazol-1-yl]-(4-methyl-piperazin-1-yl)-methanone was prepared from 5-(4-chloro-phenyl)-2-(2-ethoxy-4-methoxy-phenyl)-4-propyl-4,5-dihydro-1H-imidazole (Example 18) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 499.2477, calculated for $C_{27}H_{36}N_4O_3Cl$ $[(M+H)^+]$499.2471.

EXAMPLE 26

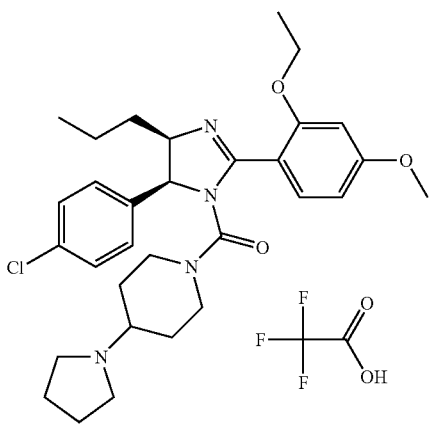

[5-(4-Chloro-phenyl)-2-(2-ethoxy-4-methoxy-phenyl)-4-propyl-4,5-dihydro-imidazol-1-yl]-(4-pyrrolidin-1-yl-piperidin-1-yl)-methanone, trifluoroacetate salt was prepared from 5-(4-chloro-phenyl)-2-(2-ethoxy-4-methoxy-phenyl)-4-propyl-4,5-dihydro-1H-imidazole (Example 18) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 553.2940, calculated for $C_{31}H_{42}N_4O_3Cl$ $[(M+H)^+]$ 553.2940.

EXAMPLE 28

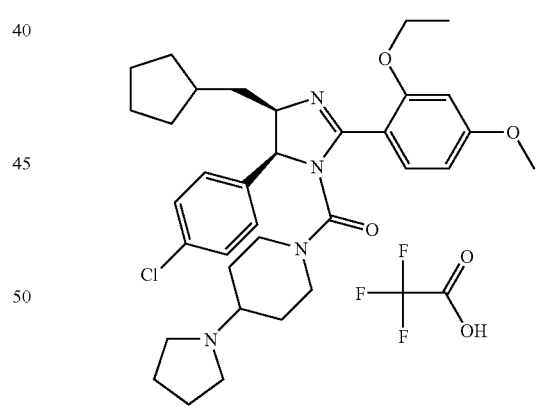

[5-(4-Chloro-phenyl)-4-cyclopentylmethyl-2-(2-ethoxy-4-methoxy-phenyl)-4,5-dihydro-imidazol-1-yl]-(4-pyrrolidin-1-yl-piperidin-1-yl)-methanone, trifluoroacetate salt was prepared from 5-(4-chloro-phenyl)-4-cyclopentylmethyl-2-(2-ethoxy-4-methoxy-phenyl)-4,5-dihydro-1H-imidazole (Example 9) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 593.3257, calculated for $C_{34}H_{35}N_4O_3Cl$ $[(M+H)^+]$593.3253.

EXAMPLE 29

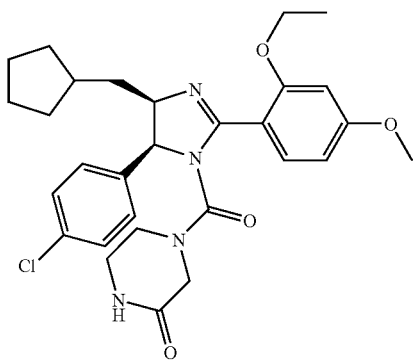

4-[5-(4-Chloro-phenyl)-4-cyclopentylmethyl-2-(2-ethoxy-4-methoxy-phenyl)-4,5-dihydro-imidazole-1-carbonyl]-piperazin-2-one was prepared from 5-(4-chloro-phenyl)-4-cyclopentylmethyl-2-(2-ethoxy-4-methoxy-phenyl)-4,5-dihydro-1H-imidazole (Example 9) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 539.2423, calculated for $C_{29}H_{36}N_4O_4Cl$ [(M+H)$^+$] 539.2420.

EXAMPLE 31

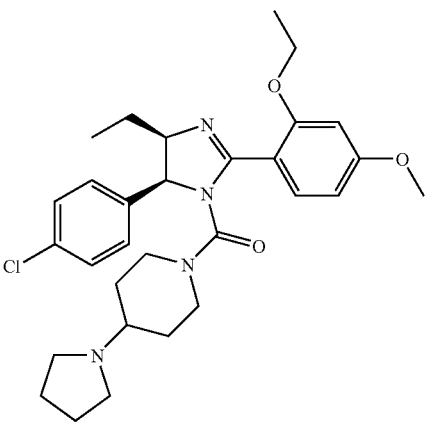

[5-(4-Chloro-phenyl)-2-(2-ethoxy-4-methoxy-phenyl)-4-ethyl-4,5-dihydro-imidazol-1-yl]-(4-pyrrolidin-1-yl-piperidin-1-yl)-methanone was prepared from 5-(4-chloro-phenyl)-2-(2-ethoxy-4-methoxy-phenyl)-4-ethyl-4,5-dihydro-1H-imidazole (Example 20) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 539.2792, calculated for $C_{30}H_{40}N_4O_3Cl$ [(M+H)$^+$]539.2784.

EXAMPLE 30

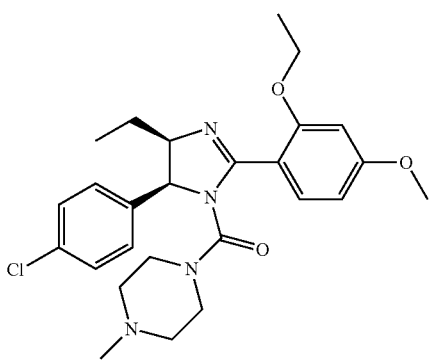

[5-(4-Chloro-phenyl)-2-(2-ethoxy-4-methoxy-phenyl)-4-ethyl-4,5-dihydro-imidazol-1-yl]-(4-methyl-piperazin-1-yl)-methanone was prepared from 5-(4-chloro-phenyl)-2-(2-ethoxy-4-methoxy-phenyl)-4-ethyl-4,5-dihydro-1H-imidazole (Example 20) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 485.2323, calculated for $C_{26}H_{34}N_4O_3Cl$ [(M+H)$^+$]485.2314.

EXAMPLE 32

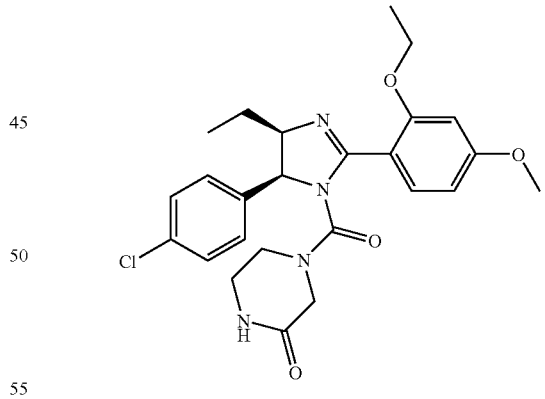

4-[5-(4-Chloro-phenyl)-2-(2-ethoxy-4-methoxy-phenyl)-4-ethyl-4,5-dihydro-imidazole-1-carbonyl]-piperazin-2-one was prepared from 5-(4-chloro-phenyl)-2-(2-ethoxy-4-methoxy-phenyl)-4-ethyl-4,5-dihydro-1H-imidazole (Example 20) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 485.1959, calculated for $C_{25}H_{30}N_4O_3Cl$ [(M+H)$^+$]485.1950.

EXAMPLE 33

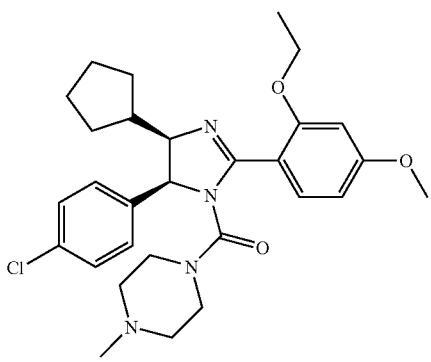

[5-(4-Chloro-phenyl)-4-cyclopentyl-2-(2-ethoxy-4-methoxy-phenyl)-4,5-dihydro-imidazol-1-yl]-(4-methyl-piperazin-1-yl)-methanone was prepared from 5-(4-chloro-phenyl)-4-cyclopentyl-2-(2-ethoxy-4-methoxy-phenyl)-4,5-dihydro-1H-imidazole, trifluoroacetate salt (Example 19) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 525.2634, calculated for $C_{29}H_{38}N_4O_3Cl$ $[(M+H)^+]$ 525.2627.

EXAMPLE 34

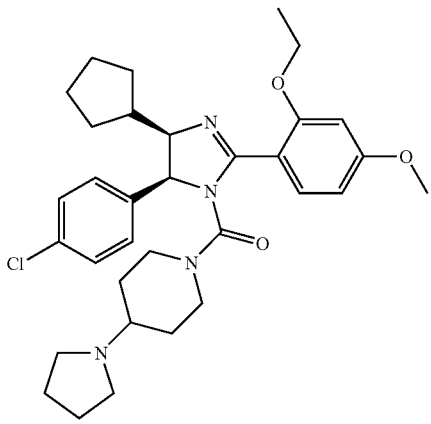

[5-(4-Chloro-phenyl)-4-cyclopentyl-2-(2-ethoxy-4-methoxy-phenyl)-4,5-dihydro-imidazol-1-yl]-(4-pyrrolidin-1-yl-piperidin-1-yl)-methanone was prepared from 5-(4-chloro-phenyl)-4-cyclopentyl-2-(2-ethoxy-4-methoxy-phenyl)-4,5-dihydro-1H-imidazole, trifluoroacetate salt (Example 19) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 579.3104, calculated for $C_{33}H_{44}N_4O_3Cl$ $[(M+H)^+]$ 579.3097.

EXAMPLE 35

4-[5-(4-Chloro-phenyl)-4-cyclopentyl-2-(2-ethoxy-4-methoxy-phenyl)-4,5-dihydro-imidazole-1-carbonyl]-piperazin-2-one was prepared from 5-(4-chloro-phenyl)-4-cyclopentyl-2-(2-ethoxy-4-methoxy-phenyl)-4,5-dihydro-1H-imidazole, trifluoroacetate salt (Example 19) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 525.2271, calculated for $C_{28}H_{34}N_4O_4Cl$ $[(M+H)^+]$ 525.2263.

EXAMPLE 36

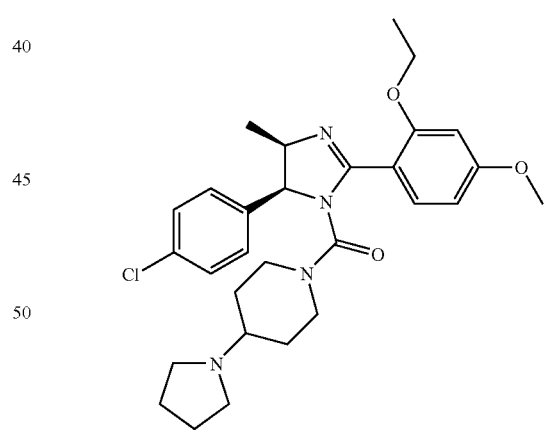

[5-(4-Chloro-phenyl)-2-(2-ethoxy-4-methoxy-phenyl)-4-methyl-4,5-dihydro-imidazol-1-yl]-(4-pyrrolidin-1-yl-piperidin-1-yl)-methanone was prepared from 5-(4-chloro-phenyl)-2-(2-ethoxy-4-methoxy-phenyl)-4-methyl-4,5-dihydro-1H-imidazole, trifluoroacetate salt (Example 17) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 525.2635, calculated for $C_{29}H_{38}N_4O_3Cl$ $[(M+H)^+]$ 525.2627.

EXAMPLE 37

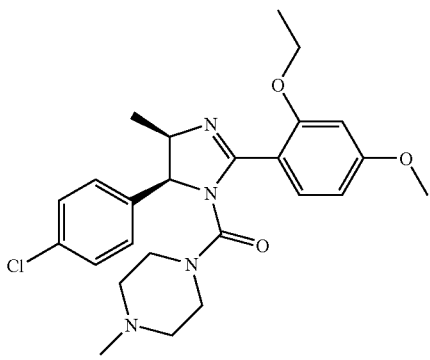

[5-(4-Chloro-phenyl)-2-(2-ethoxy-4-methoxy-phenyl)-4-methyl-4,5-dihydro-imidazol-1-yl]-(4-methyl-piperazin-1-yl)-methanone was prepared from 5-(4-chloro-phenyl)-2-(2-ethoxy-4-methoxy-phenyl)-4-methyl-4,5-dihydro-1H-imidazole, trifluoroacetate salt (Example 17) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 471.2166, calculated for $C_{25}H_{32}N_4O_3Cl$ [(M+H)$^+$] 471.2158.

EXAMPLE 38

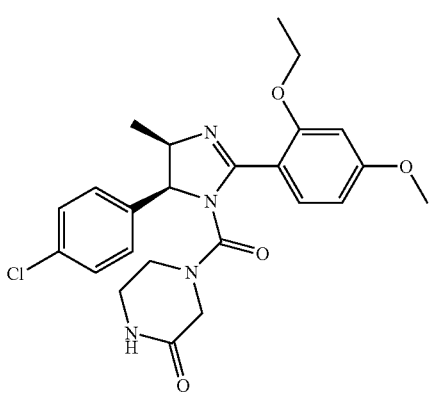

4-[5-(4-Chloro-phenyl)-2-(2-ethoxy-4-methoxy-phenyl)-4-methyl-4,5-dihydro-imidazole-1-carbonyl]-piperazin-2-one was prepared from 5-(4-chloro-phenyl)-2-(2-ethoxy-4-methoxy-phenyl)-4-methyl-4,5-dihydro-1H-imidazole, trifluoroacetate salt (Example 17) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 471.1801, calculated for $C_{24}H_{28}N_4O_4Cl$ [(M+H)$^+$] 471.1794.

EXAMPLE 39

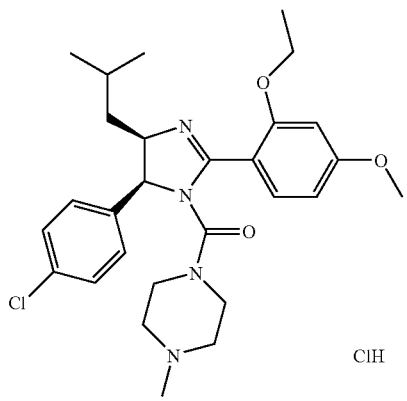

[5-(4-Chloro-phenyl)-2-(2-ethoxy-4-methoxy-phenyl)-4-isobutyl-4,5-dihydro-imidazol-1-yl]-(4-methyl-piperazin-1-yl)-methanone was prepared from 5-(4-chloro-phenyl)-2-(2-ethoxy-4-methoxy-phenyl)-4-isobutyl-4,5-dihydro-1H-imidazole (Example 10) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 513.2632, calculated for $C_{28}H_{38}N_4O_3Cl$ [(M+H)$^+$] 513.2627.

EXAMPLE 40

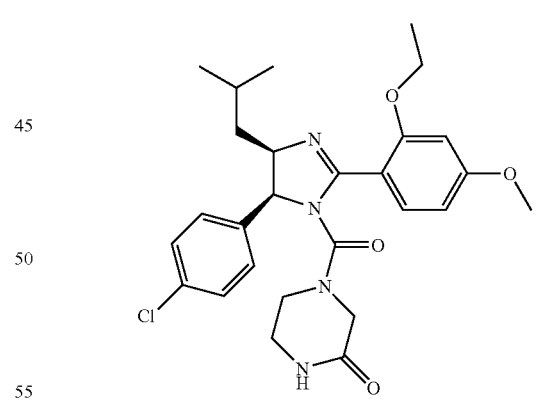

4-[5-(4-Chloro-phenyl)-2-(2-ethoxy-4-methoxy-phenyl)-4-isobutyl-4,5-dihydro-imidazole-1-carbonyl]-piperazin-2-one was prepared from 5-(4-chloro-phenyl)-2-(2-ethoxy-4-methoxy-phenyl)-4-isobutyl-4,5-dihydro-1H-imidazole (Example 10) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 513.2267, calculated for $C_{27}H_{33}N_4O_3Cl$ [(M+H)$^+$] 513.2263.

EXAMPLE 41

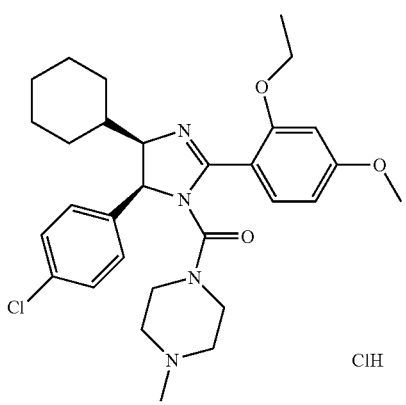

[5-(4-Chloro-phenyl)-2-(2-ethoxy-4-methoxy-phenyl)-4-isobutyl-4,5-dihydro-imidazol-1-yl]-(4-pyrrolidin-1-yl-piperidin-1-yl)-methanone was prepared from 5-(4-chloro-phenyl)-2-(2-ethoxy-4-methoxy-phenyl)-4-isobutyl-4,5-dihydro-1H-imidazole (Example 10) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 567.3103, calculated for $C_{32}H_{43}N_4O_3Cl$ [(M+H)$^+$] 567.3097.

EXAMPLE 42

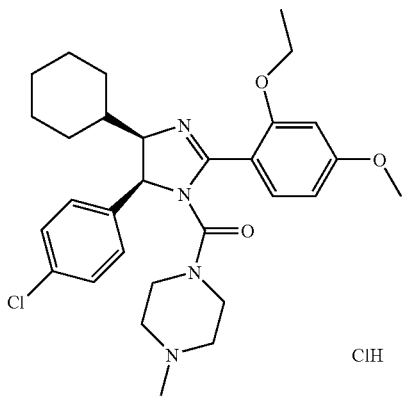

[5-(4-Chloro-phenyl)-4-cyclohexyl-2-(2-ethoxy-4-methoxy-phenyl)-4,5-dihydro-imidazol-1-yl]-(4-methyl-piperazin-1-yl)-methanone was prepared from 5-(4-chloro-phenyl)-4-cyclohexyl-2-(2-ethoxy-4-methoxy-phenyl)-4,5-dihydro-1H-imidazole (Example 11) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 539.2790, calculated for $C_{30}H_{40}N_4O_3Cl$ [(M+H)$^+$] 539.2784.

EXAMPLE 43

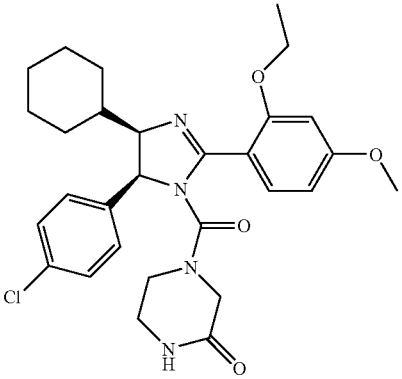

4-[5-(4-Chloro-phenyl)-4-cyclohexyl-2-(2-ethoxy-4-methoxy-phenyl)-4,5-dihydro-imidazole-1-carbonyl]-piperazin-2-one was prepared from 5-(4-chloro-phenyl)-4-cyclohexyl-2-(2-ethoxy-4-methoxy-phenyl)-4,5-dihydro-1H-imidazole (Example 11) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 539.2426, calculated for $C_{29}H_{36}N_4O_4Cl$ [(M+H)$^+$]539.2420.

EXAMPLE 44

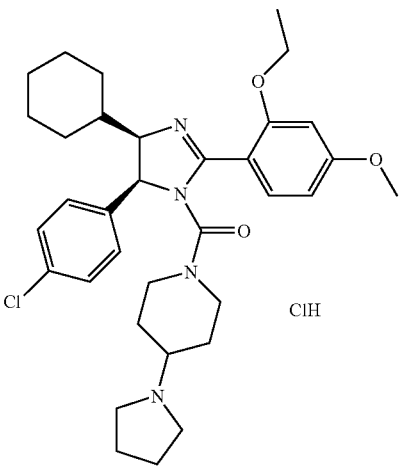

[5-(4-Chloro-phenyl)-4-cyclohexyl-2-(2-ethoxy-4-methoxy-phenyl)-4,5-dihydro-imidazol-1-yl]-(4-pyrrolidin-1-yl-piperidin-1-yl)-methanone was prepared from 5-(4-chloro-phenyl)-4-cyclohexyl-2-(2-ethoxy-4-methoxy-phenyl)-4,5-dihydro-1H-imidazole (Example 11) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 593.3260, calculated for $C_{36}H_{46}N_4O_3Cl$ [(M+H)$^+$] 593.3253.

EXAMPLE 45

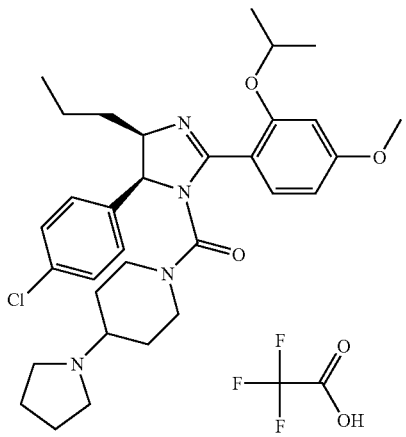

[5-(4-Chloro-phenyl)-2-(2-isopropoxy-4-methoxy-phenyl)-4-propyl-4,5-dihydro-imidazol-1-yl]-(4-pyrrolidin-1-yl-piperidin-1-yl)-methanone, trifluoroacetate salt was prepared from 5-(4-chloro-phenyl)-2-(2-isopropoxy-4-methoxy-phenyl)-4-propyl-4,5-dihydro-1H-imidazole (Example 23) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 567.3109, calculated for $C_{32}H_{44}N_4O_3Cl$ $[(M+H)^+]$ 567.3097.

EXAMPLE 46

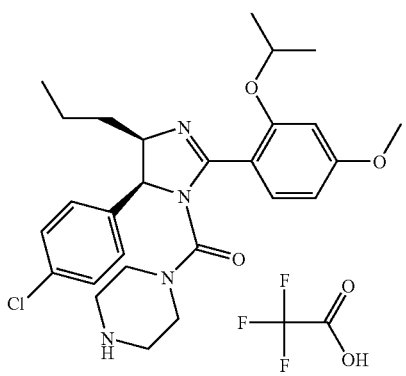

[5-(4-Chloro-phenyl)-2-(2-isopropoxy-4-methoxy-phenyl)-4-propyl-4,5-dihydro-imidazol-1-yl]-piperazin-1-yl-methanone, trifluoroacetate salt was prepared from 5-(4-chloro-phenyl)-2-(2-isopropoxy-4-methoxy-phenyl)-4-propyl-4,5-dihydro-1H-imidazole (Example 23) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 499.2475, calculated for $C_{27}H_{36}N_4O_3Cl$ $[(M+H)^+]$ 499.2471.

EXAMPLE 47

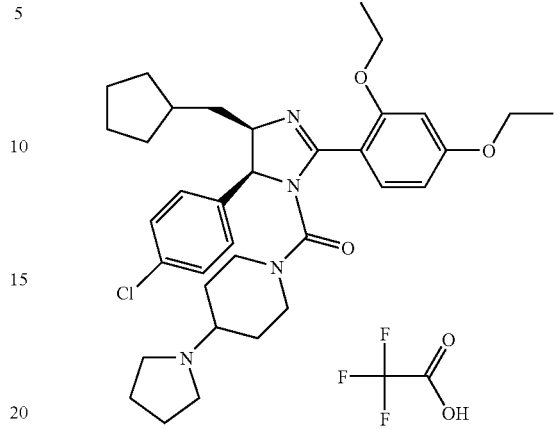

[5-(4-Chloro-phenyl)-4-cyclopentylmethyl-2-(2,4-diethoxy-phenyl)-4,5-dihydro-imidazol-1-yl]-(4-pyrrolidin-1-yl-piperidin-1-yl)-methanone, trifluoroacetate salt was prepared from 5-(4-chloro-phenyl)-4-cyclopentylmethyl-2-(2,4-diethoxy-phenyl)-4,5-dihydro-1H-imidazole (Example 21) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 607.3423, calculated for $C_{35}H_{48}N_4O_3Cl$ $[(M+H)^+]$ 607.3410.

EXAMPLE 48

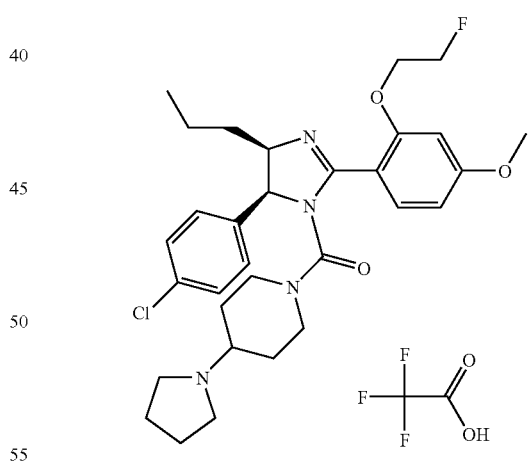

{5-(4-Chloro-phenyl)-2-[2-(2-fluoro-ethoxy)-4-methoxy-phenyl]-4-propyl-4,5-dihydro-imidazol-1-yl}-(4-pyrrolidin-1-yl-piperidin-1-yl)-methanone, trifluoroacetate salt was prepared from 5-(4-chloro-phenyl)-2-[2-(2-fluoro-ethoxy)-4-methoxy-phenyl]-4-propyl-4,5-dihydro-1H-imidazole (Example 22) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 471.2854, calculated for $C_{31}H_{41}N_4O_3Cl$ $[(M+H)^+]$ 471.2846.

EXAMPLE 49

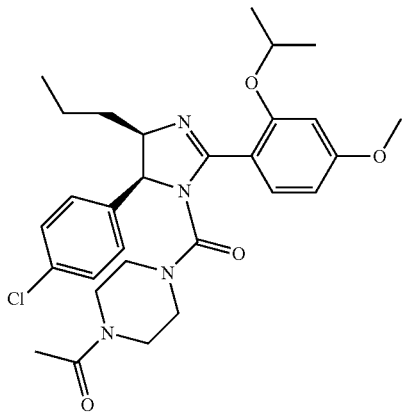

1-{4-[5-(4-Chloro-phenyl)-2-(2-isopropoxy-4-methoxy-phenyl)-4-propyl-4,5-dihydro-imidazole-1-carbonyl]-piperazin-1-yl}-ethanone was prepared from 5-(4-chloro-phenyl)-2-(2-isopropoxy-4-methoxy-phenyl)-4-propyl-4,5-dihydro-1H-imidazole (Example 23) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 541.2581, calculated for $C_{29}H_{38}N_4O_4Cl$ $[(M+H)^+]$ 541.2576.

EXAMPLE 50

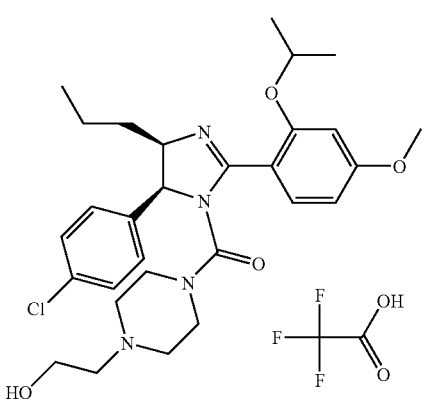

[5-(4-Chloro-phenyl)-2-(2-isopropoxy-4-methoxy-phenyl)-4-propyl-4,5-dihydro-imidazol-1-yl]-[4-(2-hydroxy-ethyl)-piperazin-1-yl]-methanone, trifluoroacetate salt was prepared from 5-(4-chloro-phenyl)-2-(2-isopropoxy-4-methoxy-phenyl)-4-propyl-4,5-dihydro-1H-imidazole (Example 23) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 543.2738, calculated for $C_{29}H_{39}N_4O_4Cl$ $[(M+H)^+]$ 543.2733.

EXAMPLE 51

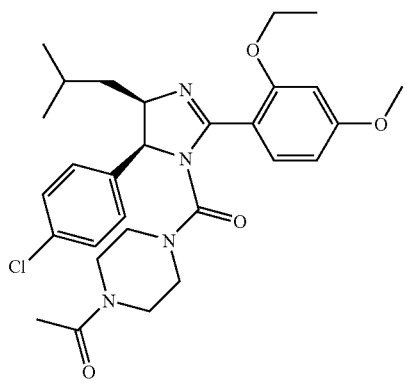

1-{4-[5-(4-Chloro-phenyl)-2-(2-ethoxy-4-methoxy-phenyl)-4-isobutyl-4,5-dihydro-imidazole-1-carbonyl]-piperazin-1-yl}-ethanone was prepared from 5-(4-chloro-phenyl)-2-(2-ethoxy-4-methoxy-phenyl)-4-isobutyl-4,5-dihydro-1H-imidazole (Example 10) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 541.2580, calculated for $C_{26}H_{32}N_4O_4Cl$ $[(M+H)^+]$ 541.2576.

EXAMPLE 52

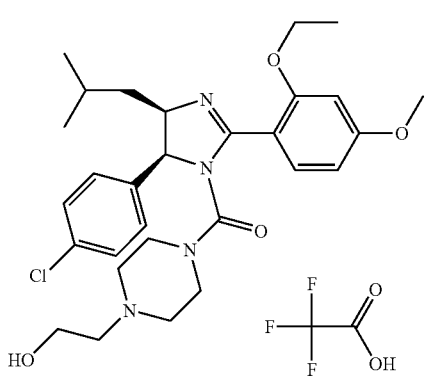

[5-(4-Chloro-phenyl)-2-(2-ethoxy-4-methoxy-phenyl)-4-isobutyl-4,5-dihydro-imidazol-1-yl]-[4-(2-hydroxy-ethyl)-piperazin-1-yl]-methanone, trifluoroacetate salt was prepared from 5-(4-chloro-phenyl)-2-(2-ethoxy-4-methoxy-phenyl)-4-isobutyl-4,5-dihydro-1H-imidazole (Example 10) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 543.2737, calculated for $C_{29}H_{40}N_4O_4Cl$ $[(M+H)^+]$ 543.2733.

EXAMPLE 53

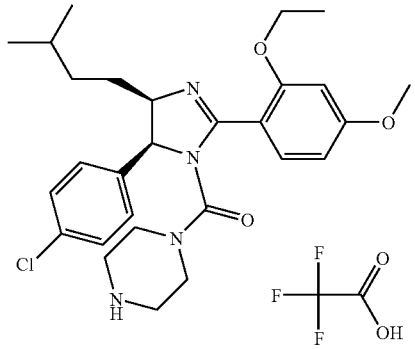

[5-(4-Chloro-phenyl)-2-(2-ethoxy-4-methoxy-phenyl)-4-(3-methyl-butyl)-4,5-dihydro-imidazol-1-yl]-piperazin-1-yl-methanone, trifluoroacetate salt was prepared from 5-(4-chloro-phenyl)-2-(2-ethoxy-4-methoxy-phenyl)-4-(3-methyl-butyl)-4,5-dihydro-1H-imidazole (Example 15) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 513.2632, calculated for $C_{28}H_{37}N_4O_3Cl$ $[(M+H)^+]$ 513.2637.

EXAMPLE 54

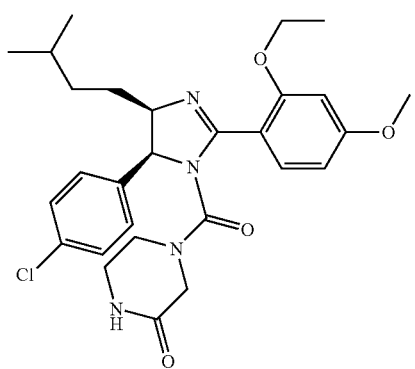

4-[5-(4-Chloro-phenyl)-2-(2-ethoxy-4-methoxy-phenyl)-4-(3-methyl-butyl)-4,5-dihydro-imidazole-1-carbonyl]-piperazin-2-one was prepared from 5-(4-chloro-phenyl)-2-(2-ethoxy-4-methoxy-phenyl)-4-(3-methyl-butyl)-4,5-dihydro-1H-imidazole (Example 15) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 527.2423, calculated for $C_{28}H_{36}N_4O_4Cl$ $[(M+H)^+]$527.2120.

EXAMPLE 55

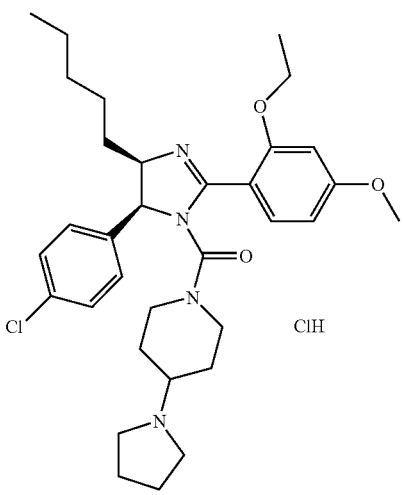

[5-(4-Chloro-phenyl)-2-(2-ethoxy-4-methoxy-phenyl)-4-pentyl-4,5-dihydro-imidazol-1-yl]-(4-pyrrolidin-1-yl-piperidin-1-yl)-methanone was prepared from 5-(4-chloro-phenyl)-2-(2-ethoxy-4-methoxy-phenyl)-4-pentyl-4,5-dihydro-1H-imidazole (Example 12) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 581.3262, calculated for $C_{33}H_{46}N_4O_3Cl$ $[(M+H)^+]581.3253$.

EXAMPLE 56

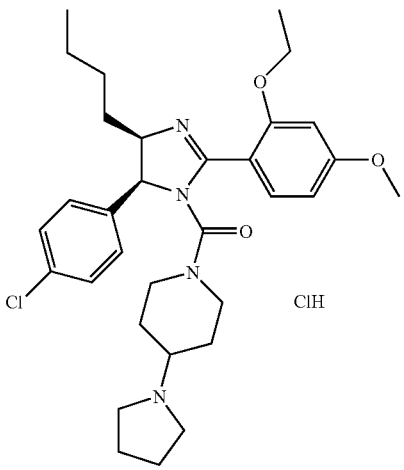

[4-Butyl-5-(4-chloro-phenyl)-2-(2-ethoxy-4-methoxy-phenyl)-4,5-dihydro-imidazol-1-yl]-(4-pyrrolidin-1-yl-piperidin-1-yl)-methanone was prepared from 4-butyl-5-(4-chloro-phenyl)-2-(2-ethoxy-4-methoxy-phenyl)-4,5-dihydro-1H-imidazole (Example 13) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 567.3106, calculated for $C_{32}H_{44}N_4O_3Cl$ $[(M+H)^+]$ 567.3097.

EXAMPLE 57

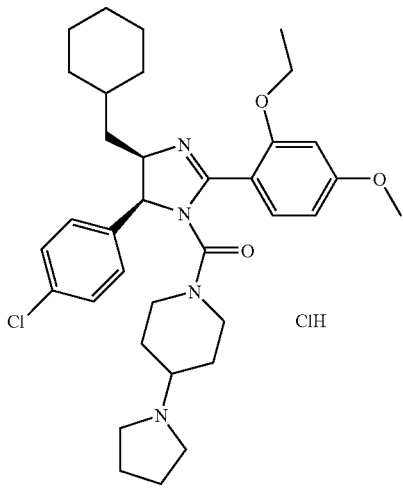

[5-(4-Chloro-phenyl)-4-cyclohexylmethyl-2-(2-ethoxy-4-methoxy-phenyl)-4,5-dihydro-imidazol-1-yl]-(4-pyrrolidin-1-yl-piperidin-1-yl)-methanone was prepared from 5-(4-chloro-phenyl)-4-cyclohexylmethyl-2-(2-ethoxy-4-methoxy-phenyl)-4,5-dihydro-1H-imidazole (Example 14) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 607.3419, calculated for $C_{35}H_{48}N_4O_3Cl$ [(M+H)$^+$] 607.3410.

EXAMPLE 58

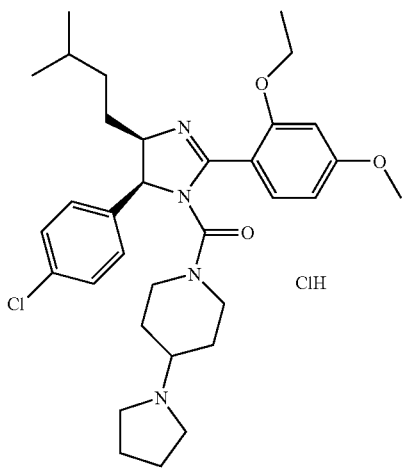

[5-(4-Chloro-phenyl)-2-(2-ethoxy-4-methoxy-phenyl)-4-(3-methyl-butyl)-4,5-dihydro-imidazol-1-yl]-(4-pyrrolidin-1-yl-piperidin-1-yl)-methanone was prepared from 5-(4-chloro-phenyl)-2-(2-ethoxy-4-methoxy-phenyl)-4-(3-methyl-butyl)-4,5-dihydro-1H-imidazole (Example 15) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 581.3261, calculated for $C_{33}H_{46}N_4O_3Cl$ [(M+H)$^+$] 581.3253.

EXAMPLE 59

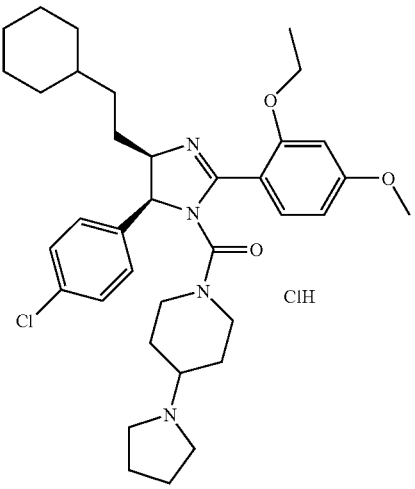

[5-(4-Chloro-phenyl)-4-(2-cyclohexyl-ethyl)-2-(2-ethoxy-4-methoxy-phenyl)-4,5-dihydro-imidazol-1-yl]-(4-pyrrolidin-1-yl-piperidin-1-yl)-methanone was prepared from 5-(4-chloro-phenyl)-4-(2-cyclohexyl-ethyl)-2-(2-ethoxy-4-methoxy-phenyl)-4,5-dihydro-1H-imidazole (Example 16) in an analogous manner as described for the preparation of [5-(4-chloro-phenyl)-4-cyclopentylmethyl-2-(2-ethoxy-4-methoxy-phenyl)-4,5-dihydro-imidazol-1-yl]-(4-methyl-piperazin-1-yl)-methanone (Example 24). HR-MS (ES, m/z) observed 621.3573, calculated for $C_{36}H_{50}N_4O_3Cl$ [(M+H)$^+$]621.3566.

EXAMPLE 60

In Vitro Activity Assay

The ability of the compounds to inhibit the interaction between p53 and MDM2 proteins was measured by an ELISA (Enzyme-Linked Immuno Sorbent Assay) in which recombinant GST-tagged MDM2 binds to a peptide that resembles the MDM2-interacting region of p53 (Böttger et al., J. Mol. Bio. 1997, Vol. 269, pgs. 744–756). This peptide was immobilized to the surface of a 96 well plate via N-terminal biotin which binds to streptavidin-coated wells. MDM2 was added to each well in the presence of anti-MDM2 mouse monoclonal antibody (SMP-14, Santa Cruz Biotech). After removal of the unbound MDM2 protein, a peroxydase-linked secondary antibody (anti-mouse IgG, Roche Molecular Biochemicals) and the amount of peptide-bound MDM2 was determined colorimetrically by the addition of a peroxydase substrate (MTB Microwell Peroxydase Substrate System, Kirkegaard & Perry Labs).

Test plates were prepared by coating with streptavidin (5 mg/ml in PBS) for 2 hours followed by a PBS (phosphate-buffered saline) wash and overnight blocking with 150 μl of blocking buffer containing 2 mg/ml bovine serum albumin (Sigma) and 0.05% Tween 20 (Sigma) in PBS at 4° C. Biotinylated peptide (1 μM) was added to each well in 50 μl of blocking buffer and washed extensively after 1 h incubation. Test compounds were diluted in a separate 96 well plate and added in triplicate to a compound incubation plate containing a mix of the MDM2 protein and anti-MDM2 antibody. After 20 min incubation, the content of the plate was transferred to the test plate and incubated for an additional 1 hour. The secondary anti-mouse IgG antibody was added to the test plate proceeded and followed by a triple wash with 0.05% Tween 20 in PBS. Finally, peroxydase substrate was added to each well and the absorption was read using a plate reader (MR7000, Dynatech) at 450 nm. The inhibitory activity of the test compounds was measured as a percentage of the bound MDM2 in treated vs. untreated wells and $IC_{50}$ was calculated. $IC_{50}$s showing biological activity that applies to compounds of the subject matter of this invention ranges from about 0.5 μM to about 150 μM. Specific data for some examples are as follows:

| Example | IC50 (μM) |
|---------|-----------|
| 26 | 45.0 |
| 24 | 13.2 |
| 28 | 5.5 |
| 55 | 0.7 |

What is claimed is:

1. At least one compound selected from a compound of formula I

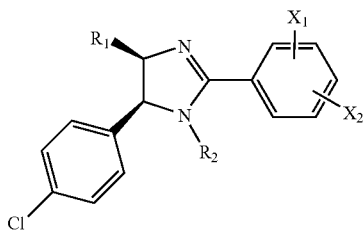

wherein $X_1$ and $X_2$ are each independently selected from the group consisting of hydrogen, $-OR_3$, $-SR_4$, $-NR_5R_6$, $-CONR_5R_6$, $-COOR_7$, halogen, nitro, trifluoromethyl, lower alkyl, lower alkyl substituted by $R_8$, cycloalkyl;

$R_1$ is selected from the group consisting of C1–C8 alkyl, C1–C4 alkyl attached to C4–C8 cycloalkyl and C4–C8 cycloalkyl;

$R_2$ is $-C=OR_9$;

$R_3$ is selected from the group consisting of hydrogen, lower alkyl, lower alkyl substituted by $R_8$, and cycloalkyl;

$R_4$ is selected from the group consisting of hydrogen and lower alkyl;

$R_5$ and $R_6$ are each independently selected from the group consisting of hydrogen, lower alkyl and cycloalkyl; or $R_5$ and $R_6$ together with the two carbon atoms and the bonds between them from the benzene ring to which they are substituted form a ring selected from a 5- or 6-membered unsaturated ring or a 5- or 6-membered saturated ring that contains at least one hetero atom selected from S, N and O;

$R_7$ is selected from the group consisting of hydrogen, lower alkyl and cycloalkyl;

$R_8$ is selected from the group consisting of $-CONR_5R_6$, $-NR_5R_6$, $COOR_7$, aryl, halogen, lower alkoxy, morpholinyl and heterocycles;

$R_9$ is selected from C1–C4 alkyl, $-CH=CHCOOH$, $-NHCH_2CH_2R_{10}$, $-N(CH_2CH_2OH)CH_2CH_2OH$, $-N(CH_3)CH_2CH_2NCH_3$, $-N(CH_3)CH_2CH_2N(CH_3)CH_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, $-C=O-R_{11}$, $-OH$, lower alkyl substituted with hydroxy, lower alkyl substituted with $-NH_2$, N-lower alkyl, $-SO_2CH_3$, $=O$, $-CH_2C=OCH_3$, and 5- and 6-membered saturated rings containing at least one hetero atom selected from S, N and O, $R_{10}$ is selected from the group consisting of $-N(CH_3)CH_3$, $-NHCH_2CH_2NH_2$, $-NH_2$, morpholinyl and piperazinyl; and $R_{11}$ is selected from H, lower alkyl, $-NH_2$, $-N$-lower alkyl, lower alkyl substituted with hydroxy, and lower alkyl substituted with $NH_2$, or a pharmaceutically acceptable salt or ester thereof.

2. The compound of claim 1 wherein R1 is $C_1$–$C_8$ alkyl.

3. The compound of claim 1 wherein R1 is $C_1$–$C_4$ alkyl attached to $C_4$–$C_8$ cycloalkyl.

4. The compound of claim 1 wherein R1 is $C_4$–$C_8$ cycloalkyl.

5. The compound of claim 1 wherein $X_1$ is selected from the group consisting of ethoxy, isopropoxy, 2-fluoroethoxy and $-OCH_2CF_3$ at the ortho position.

6. The compound of claim 1 wherein $X_2$ is selected from the group consisting of methoxy, ethoxy and trifluoromethyl at the para position.

7. The compound of claim 1 wherein $R_9$ is selected from the group consisting of morpholinyl, piperazinyl, piperadinyl, cyclopentyl, cyclohexyl, thiophenyl, isoxazlyl, furanyl, piperazinyl substituted with at least one group selected from C1–C3 alkyl, $-C1-C2$ alkoxy, $-C=OCH_3$, $-SO_2CH_3$, $-C=O$, $-OH$, $-CH_2NH_2$, $-C=OCH_2NH_2$, $-C=OCH_2OH$, $-C=OC(OH)CH_2OH$, $-CH_2C(OH)-CH_2OH$, $-C=ON(CH_2-)_2$, $-C=ONH2$, $-C=ON(CH_3)CH_3$, $-C=OCH(CH_3)_2$, $-CH_2C=OCH_3$, $-CH_2CH(OH)CH_3$, $-CH(CH_3)CH(OH)CH_3$ and piperidinyl substituted with at least one group selected from C1–C3 alkyl, $-C1-C2$ alkoxy, $-C=OCH_3$, $-SO_2CH_3$, $-C=O$, $-OH$, $-CH_2NH_2$, $-C=OCH_2NH_2$, $-C=OCH_2OH$, $-C=OC(OH)CH_2OH$, $-CH_2C(OH) CH_2OH$, $-C=ON(CH_2)_2$, $-C=ONH_2$, and $-C=ON(CH_3)CH_3$, $-N(CH_3)CH_3$, pyrrolidinyl and piperadinyl.

8. The compound of claim 1 that is selected from the group consisting of:

[5-(4-Chloro-phenyl)-4-cyclopentylmethyl-2-(2-ethoxy-4-methoxy-phenyl)-4,5-dihydro-imidazol-1-yl]-(4-methyl-piperazin-1-yl)-methanone, trifluoroacetate salt;

4-[5-(4-Chloro-phenyl)-2-(2-ethoxy-4-methoxy-phenyl)-4-propyl-4,5-dihydro-imidazole-1-carbonyl]-piperazin-2-one;

[5-(4-Chloro-phenyl)-2-(2-ethoxy-4-methoxy-phenyl)-4-propyl-4,5-dihydro-imidazol-1-yl]-(4-pyrrolidin-1-yl-piperidin-1-yl)-methanone, trifluoroacetate salt;

[5-(4-Chloro-phenyl)-2-(2-ethoxy-4-methoxy-phenyl)-4-propyl-4,5-dihydro-imidazol-1-yl]-(4-methyl-piperazin-1-yl)-methanone; and

[5-(4-Chloro-phenyl)-4-cyclopentylmethyl-2-(2-ethoxy-4-methoxy-phenyl)-4,5-dihydro-imidazol-1-yl]-(4-pyrrolidin-1-yl-piperidin-1-yl)-methanone, trifluoroacetate salt.

9. The compound of claim 1 that is selected from the group consisting of:
4-[5-(4-Chloro-phenyl)-4-cyclopentylmethyl-2-(2-ethoxy-4-methoxy-phenyl)-4,5-dihydro-imidazole-1-carbonyl]-piperazin-2-one;
[5-(4-Chloro-phenyl)-2-(2-ethoxy-4-methoxy-phenyl)-4-ethyl-4,5-dihydro-imidazol-1-yl]-(4-methyl-piperazin-1-yl)-methanone;
[5-(4-Chloro-phenyl)-2-(2-ethoxy-4-methoxy-phenyl)-4-ethyl-4,5-dihydro-imidazol-1-yl]-(4-pyrrolidin-1-yl-piperidin-1-yl)-methanone;
4-[5-(4-Chloro-phenyl)-2-(2-ethoxy-4-methoxy-phenyl)-4-ethyl-4,5-dihydro-imidazole-1-carbonyl]-piperazin-2-one;
[5-(4-Chloro-phenyl)-4-cyclopentyl-2-(2-ethoxy-4-methoxy-phenyl)-4,5-dihydro-imidazol-1-yl]-(4-methyl-piperazin-1-yl)-methanone;
[5-(4-Chloro-phenyl)-4-cyclopentyl-2-(2-ethoxy-4-methoxy-phenyl)-4,5-dihydro-imidazol-1-yl]-(4-pyrrolidin-1-yl-piperidin-1-yl)-methanone;
4-[5-(4-Chloro-phenyl)-4-cyclopentyl-2-(2-ethoxy-4-methoxy-phenyl)-4,5-dihydro-imidazole-1-carbonyl]-piperazin-2-one;
[5-(4-Chloro-phenyl)-2-(2-ethoxy-4-methoxy-phenyl)-4-methyl-4,5-dihydro-imidazol-1-yl]-(4-pyrrolidin-1-yl-piperidin-1-yl)-methanone;
[5-(4-Chloro-phenyl)-2-(2-ethoxy-4-methoxy-phenyl)-4-methyl-4,5-dihydro-imidazol-1-yl]-(4-methyl-piperazin-1-yl)-methanone; and
4-[5-(4-Chloro-phenyl)-2-(2-ethoxy-4-methoxy-phenyl)-4-methyl-4,5-dihydro-imidazole-1-carbonyl]-piperazin-2-one.

10. The compound of claim 1 that is selected from the group consisting of:
[5-(4-Chloro-phenyl)-2-(2-ethoxy-4-methoxy-phenyl)-4-isobutyl-4,5-dihydro-imidazol-1-yl]-(4-methyl-piperazin-1-yl)-methanone;
4-[5-(4-Chloro-phenyl)-2-(2-ethoxy-4-methoxy-phenyl)-4-isobutyl-4,5-dihydro-imidazole-1-carbonyl]-piperazin-2-one;
[5-(4-Chloro-phenyl)-2-(2-ethoxy-4-methoxy-phenyl)-4-isobutyl-4,5-dihydro-imidazol-1-yl]-(4-pyrrolidin-1-yl-piperidin-1-yl)-methanone;
[5-(4-Chloro-phenyl)-4-cyclohexyl-2-(2-ethoxy-4-methoxy-phenyl)-4,5-dihydro-imidazol-1-yl]-(4-methyl-piperazin-1-yl)-methanone;
4-[5-(4-Chloro-phenyl)-4-cyclohexyl-2-(2-ethoxy-4-methoxy-phenyl)-4,5-dihydro-imidazole-1-carbonyl]-piperazin-2-one;
[5-(4-Chloro-phenyl)-4-cyclohexyl-2-(2-ethoxy-4-methoxy-phenyl)-4,5-dihydro-imidazol-1-yl]-(4-pyrrolidin-1-yl-piperidin-1-yl)-methanone;
[5-(4-Chloro-phenyl)-2-(2-isopropoxy-4-methoxy-phenyl)-4-propyl-4,5-dihydro-imidazol-1-yl]-(4-pyrrolidin-1-yl-piperidin-1-yl)-methanone, trifluoroacetate salt;
[5-(4-Chloro-phenyl)-2-(2-isopropoxy-4-methoxy-phenyl)-4-propyl-4,5-dihydro-imidazol-1-yl]-piperazin-1-yl-methanone, trifluoroacetate salt;
[5-(4-Chloro-phenyl)-4-cyclopentylmethyl-2-(2,4-diethoxy-phenyl)-4,5-dihydro-imidazol-1-yl]-(4-pyrrolidin-1-yl-piperidin-1-yl)-methanone, trifluoroacetate salt; and
{5-(4-Chloro-phenyl)-2-[2-(2-fluoro-ethoxy)-4-methoxy-phenyl]-4-propyl-4,5-dihydro-imidazol-1-yl}-(4-pyrrolidin-1-yl-piperidin-1-yl)-methanone, trifluoroacetate salt.

11. The compound of claim 1 that is selected from the group consisting of:
1-{4-[5-(4-Chloro-phenyl)-2-(2-isopropoxy-4-methoxy-phenyl)-4-propyl-4,5-dihydro-imidazole-1-carbonyl]-piperazin-1-yl}-ethanone;
[5-(4-Chloro-phenyl)-2-(2-isopropoxy-4-methoxy-phenyl)-4-propyl-4,5-dihydro-imidazol-1-yl]-[4-(2-hydroxy-ethyl)-piperazin-1-yl]-methanone, trifluoroacetate salt;
1-{4-[5-(4-Chloro-phenyl)-2-(2-ethoxy-4-methoxy-phenyl)-4-isobutyl-4,5-dihydro-imidazole-1-carbonyl]-piperazin-1-yl}-ethanone;
[5-(4-Chloro-phenyl)-2-(2-ethoxy-4-methoxy-phenyl)-4-isobutyl-4,5-dihydro-imidazol-1-yl]-[4-(2-hydroxy-ethyl)-piperazin-1-yl]-methanone, trifluoroacetate salt;
[5-(4-Chloro-phenyl)-2-(2-ethoxy-4-methoxy-phenyl)-4-(3-methyl-butyl)-4,5-dihydro-imidazol-1-yl]-piperazin-1-yl-methanone, trifluoroacetate salt;
4-[5-(4-Chloro-phenyl)-2-(2-ethoxy-4-methoxy-phenyl)-4-(3-methyl-butyl)-4,5-dihydro-imidazole-1-carbonyl]-piperazin-2-one;
[5-(4-Chloro-phenyl)-2-(2-ethoxy-4-methoxy-phenyl)-4-pentyl-4,5-dihydro-imidazol-1-yl]-(4-pyrrolidin-1-yl-piperidin-1-yl)-methanone;
[4-Butyl-5-(4-chloro-phenyl)-2-(2-ethoxy-4-methoxy-phenyl)-4,5-dihydro-imidazol-1-yl]-(4-pyrrolidin-1-yl-piperidin-1-yl)-methanone;
[5-(4-Chloro-phenyl)-4-cyclohexylmethyl-2-(2-ethoxy-4-methoxy-phenyl)-4,5-dihydro-imidazol-1-yl]-(4-pyrrolidin-1-yl-piperidin-1-yl)-methanone;
[5-(4-Chloro-phenyl)-2-(2-ethoxy-4-methoxy-phenyl)-4-(3-methyl-butyl)-4,5-dihydro-imidazol-1-yl]-(4-pyrrolidin-1-yl-piperidin-1-yl)-methanone; and
[5-(4-Chloro-phenyl)-4-(2-cyclohexyl-ethyl)-2-(2-ethoxy-4-methoxy-phenyl)-4,5-dihydro-imidazol-1-yl]-(4-pyrrolidin-1-yl-piperidin-1-yl)-methanone.

12. A pharmaceutical composition which comprises at least one compound selected from a compound of formula I

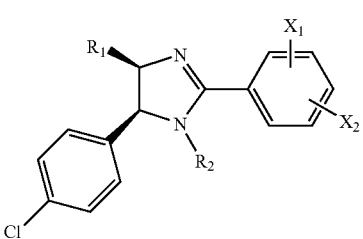

wherein
$X_1$ and $X_2$ are each independently selected from the group consisting of hydrogen, —$OR_3$, —$SR_4$, —$NR_5R_6$, —$CONR_5R_6$, —$COOR_7$, halogen, nitro, trifluoromethyl, lower alkyl, lower alkyl substituted by $R_8$, cycloalkyl;
$R_1$ is selected from the group consisting of C1–C8 alkyl, C1–C4 alkyl attached to C4–C8 cycloalkyl and C4–C8 cycloalkyl;
$R_2$ is —C=$OR_9$;

$R_3$ is selected from the group consisting of hydrogen, lower alkyl, lower alkyl substituted by $R_8$, and cycloalkyl;

$R_4$ is selected from the group consisting of hydrogen and lower alkyl;

$R_5$ and $R_6$ are each independently selected from the group consisting of hydrogen, lower alkyl and cycloalkyl; or $R_5$ and $R_6$ together with the two carbon atoms and the bonds between them from the benzene ring to which they are substituted form a ring selected from a 5- or 6-membered unsaturated ring or a 5- or 6-membered saturated ring that contains at least one hetero atom selected from S, N and O;

$R_7$ is selected from the group consisting of hydrogen, lower alkyl and cycloalkyl;

$R_8$ is selected from the group consisting of —$CONR_5R_6$, —$NR_5R_6$, $COOR_7$, aryl, halogen, lower alkoxy, morpholinyl and heterocycles;

$R_9$ is selected from C1–C4 alkyl, —CH=CHCOOH, —$NHCH_2CH_2R_{10}$, —$N(CH_2CH_2OH)CH_2CH_2OH$, —$N(CH_3)CH_2CH_2NCH_3$, —$N(CH_3)CH_2CH_2N(CH_3)CH_3$, saturated 4-, 5- and 6-membered rings, and saturated and unsaturated 5- and 6-membered rings containing at least one hetero atom wherein the hetero atom is selected from S, N and O and being optionally substituted with a group selected from lower alkyl, —C=O—$R_{11}$, —OH, lower alkyl substituted with hydroxy, lower alkyl substituted with —$NH_2$, N-lower alkyl, —$SO_2CH_3$, =O, —$CH_2C$=$OCH_3$, and 5- and 6-membered saturated rings containing at least one hetero atom selected from S, N and O, $R_{10}$ is selected from the group consisting of —$N(CH_3)CH_3$, —$NHCH_2CH_2NH_2$, —$NH_2$, morpholinyl and piperazinyl; and $R_{11}$ is selected from H, lower alkyl, —$NH_2$, —N-lower alkyl, lower alkyl substituted with hydroxy, and lower alkyl substituted with $NH_2$, or a pharmaceutically acceptable salt or ester thereof, and a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,132,421 B2 | Page 1 of 1 |
| APPLICATION NO. | : 10/868092 | |
| DATED | : November 7, 2006 | |
| INVENTOR(S) | : Nader Fotouhi et al. | |

It is certified that error appears in the above-identified patent and that said Letters Patent is hereby corrected as shown below:

Title Page, (75) Inventors: delete "Emily Aijun Liu, Basking Ridge, NJ (US)" and insert -- Emily Aijun Liu, Nutley, NJ (US) --

Signed and Sealed this

Twenty-first Day of August, 2007

JON W. DUDAS
*Director of the United States Patent and Trademark Office*